US010632235B2

(12) United States Patent
Argenta et al.

(10) Patent No.: US 10,632,235 B2
(45) Date of Patent: Apr. 28, 2020

(54) DEVICES AND METHODS FOR TREATING SPINAL CORD TISSUE

(71) Applicant: Wake Forest University Health Sciences, Winston-Salem, NC (US)

(72) Inventors: Louis C Argenta, Winston-Salem, NC (US); David L Carroll, Winston-Salem, NC (US); Nicole H Levi, Winston-Salem, NC (US); Jie Liu, Woodbury, MN (US); Michael J Morykwas, Winston-Salem, NC (US); Stephen Tatter, Winston-Salem, NC (US); William D Wagner, Clemmons, NC (US)

(73) Assignee: WAKE FOREST UNIVERSITY HEALTH SCIENCES, Winston-Salem, NC (US)

( * ) Notice: Subject to any disclaimer, the term of this patent is extended or adjusted under 35 U.S.C. 154(b) by 36 days.

(21) Appl. No.: 15/700,667

(22) Filed: Sep. 11, 2017

(65) Prior Publication Data

US 2017/0368242 A1    Dec. 28, 2017

Related U.S. Application Data

(60) Continuation of application No. 14/458,790, filed on Aug. 13, 2014, now abandoned, which is a division of
(Continued)

(51) Int. Cl.
*A61M 1/00* (2006.01)
*A61F 13/00* (2006.01)

(52) U.S. Cl.
CPC ..... *A61M 1/0088* (2013.01); *A61F 13/00021* (2013.01); *A61M 1/0023* (2013.01); *A61M 2210/1003* (2013.01)

(58) Field of Classification Search
CPC .............. A61M 1/0023; A61M 1/0088; A61M 2210/1003; A61F 13/00021
See application file for complete search history.

(56) References Cited

U.S. PATENT DOCUMENTS

| 4,187,852 A | 2/1980 | Urry |
| 4,221,215 A * | 9/1980 | Mandelbaum ...... A61M 16/047 |
| | | 128/DIG. 26 |

(Continued)

FOREIGN PATENT DOCUMENTS

| DE | 4439240 | 5/1996 |
| GB | 712939 | 8/1954 |

(Continued)

OTHER PUBLICATIONS

Dong, et al.; Performance of an in situ formed bioactive hydrogel dressing from a PEG-based hyperbranched multifunctional copolymer; Acta Biomaterialia; 10 (2014) 2076 2085.
(Continued)

*Primary Examiner* — Quynh-Nhu H. Vu
(74) *Attorney, Agent, or Firm* — Niels Haun; Dann, Dorfman, Herrell and Skillman, P.C.

(57) ABSTRACT

The present invention provides devices and methods that treat damaged spinal cord tissue, such as spinal tissue damaged by disease, infection, or trauma, which may lead to the presence of swelling, compression, and compromised blood flow secondary to interstitial edema.

10 Claims, 8 Drawing Sheets

Related U.S. Application Data application No. 12/248,346, filed on Oct. 9, 2008, now Pat. No. 8,834,520.

(60) Provisional application No. 61/088,558, filed on Aug. 13, 2008, provisional application No. 61/081,997, filed on Jul. 18, 2008, provisional application No. 60/978,884, filed on Oct. 10, 2007.

(56) References Cited

U.S. PATENT DOCUMENTS

| | | | |
|---|---|---|---|
| 4,661,530 A | 4/1987 | Gogolewski | |
| 4,841,962 A | 6/1989 | Berg | |
| 4,906,233 A * | 3/1990 | Moriuchi | A61M 25/02 128/DIG. 26 |
| 5,024,841 A | 6/1991 | Chu | |
| 5,490,962 A | 2/1996 | Cima | |
| 5,516,396 A | 5/1996 | Maurer | |
| 5,607,590 A | 3/1997 | Shimizu | |
| 5,662,625 A | 9/1997 | Westwood | |
| 5,736,372 A | 4/1998 | Vacanti | |
| 5,766,618 A | 6/1998 | Laurencin | |
| 6,095,148 A | 8/2000 | Shastri | |
| 6,106,913 A | 8/2000 | Scardino | |
| 6,695,823 B1 * | 2/2004 | Lina | A61F 13/0203 602/43 |
| 7,216,651 B2 | 5/2007 | Argenta | |
| 7,722,894 B2 | 5/2010 | Wang | |
| 8,267,960 B2 | 9/2012 | Argenta | |
| 8,632,523 B2 | 1/2014 | Eriksson | |
| 8,764,794 B2 | 7/2014 | Argenta | |
| 8,834,520 B2 | 9/2014 | Argenta | |
| 8,932,620 B2 | 1/2015 | Lelkes | |
| 9,289,193 B2 | 3/2016 | Argenta | |
| 1,007,631 A1 | 9/2018 | Argenta | |
| 2002/0004556 A1 | 1/2002 | Foulger | |
| 2003/0027332 A1 | 2/2003 | Lafrance | |
| 2003/0108587 A1 * | 6/2003 | Orgill | A61L 15/42 424/423 |
| 2003/0109855 A1 | 6/2003 | Solem | |
| 2003/0118692 A1 | 6/2003 | Wang | |
| 2003/0208149 A1 * | 11/2003 | Coffey | A61F 13/02 602/48 |
| 2004/0039391 A1 * | 2/2004 | Argenta | A61B 17/88 606/86 R |
| 2004/0210009 A1 | 10/2004 | Kobayashi | |
| 2005/0063939 A1 | 3/2005 | Ameer | |
| 2006/0079852 A1 * | 4/2006 | Bubb | A61F 13/0203 604/317 |
| 2006/0263417 A1 | 11/2006 | Lelkes | |
| 2006/0293169 A1 | 12/2006 | Srinivasan | |
| 2007/0071790 A1 | 3/2007 | Ameer | |
| 2007/0155010 A1 | 7/2007 | Farnsworth | |
| 2007/0185426 A1 | 8/2007 | Ambrosio | |
| 2007/0208420 A1 | 9/2007 | Ameer | |
| 2008/0009830 A1 | 1/2008 | Fujimoto | |
| 2008/0031934 A1 | 2/2008 | MacPhee | |
| 2008/0102054 A1 * | 5/2008 | Faustman | A61K 35/54 424/85.2 |
| 2008/0112998 A1 | 5/2008 | Wang | |
| 2008/0147156 A1 | 6/2008 | Imran | |
| 2008/0153796 A1 * | 6/2008 | Occleston | A61K 31/56 514/182 |
| 2009/0011486 A1 | 1/2009 | Bettinger | |
| 2009/0093565 A1 | 4/2009 | Yang | |
| 2009/0148945 A1 | 6/2009 | Ameer | |
| 2009/0187259 A1 | 7/2009 | Argenta | |
| 2009/0254120 A1 | 10/2009 | Argenta | |
| 2009/0295644 A1 | 12/2009 | Curran | |
| 2009/0325859 A1 | 12/2009 | Ameer | |
| 2010/0196478 A1 | 8/2010 | Masters | |
| 2010/0221304 A1 | 9/2010 | Tan | |
| 2011/0052646 A1 | 3/2011 | Kaigler | |
| 2011/0129436 A1 | 6/2011 | Pryor | |
| 2011/0262489 A1 | 10/2011 | Zhao | |
| 2012/0016325 A1 | 1/2012 | Pinto | |
| 2012/0265297 A1 | 10/2012 | Altman | |
| 2014/0079759 A1 | 3/2014 | Patel | |

FOREIGN PATENT DOCUMENTS

| | | |
|---|---|---|
| JP | 1004629 | 1/1989 |
| JP | 2008099565 | 5/2008 |
| WO | 199000060 | 1/1990 |
| WO | 9918892 | 4/1999 |
| WO | 2000061206 | 10/2000 |
| WO | 03026489 | 4/2003 |
| WO | 2007060433 | 5/2007 |
| WO | 2012004627 | 1/2012 |
| WO | 2012078472 | 6/2012 |

OTHER PUBLICATIONS

Moues et al.,; The role of topical negative pressure in wound repair: Expression of biochemical markers in wound fluid during wound healing; Wound Repair and Regeneration; pp. 448-494.

Seol et al.; Biocompatibility and preclinical feasibility tests of a temperature-sensitive hydrogel for the purpose of surgical wound pain control and cartilage; repair Journal of Biomedical Materials Research B: Applied Biomaterials | Nov. 2013 vol. 101B, Issue 8; pp. 1508-1515.

Casper el al. "Coating Electrospun Collagen and Gelatin Fibers with Perlecan Domain I for Increased Growth Factor Binding" Biomacromolecules, vol. 8 Issue 4 (Feb. 28, 2007): pp. 1116-1123.

Zhang et al. "In vitro evaluation of electrospun silk fibroin scaffolds for vascular cell growth" Biomalerials, vol. 29 Issue 14 (Feb. 14, 2008): pp. 2217-2227.

Lee et al. "Nanofiber alignment and direction of mechanical strain affect the ECM production of human ACL fibroblast" Biomaterials, vol. 26 Issue 11 (Jun. 11, 2004): pp. 1261-1270.

Yeo et al. "Collagen-Based Biomimetic Nanofibrous Scaffolds: Preparation and Characterization of Collagen/Silk Fibroin Bicomponent Nanofibrous Structures" Biomacromolecules, vol. 9 Issue 4 (Mar. 8, 2008): pp. 1106-1116.

Zhang et al.; "Electrospun Biomimic Nanofibrous Scaffolds of Silk Fibroin/Hyuronic Acid for Tissue Engineering"; Journal of Biomaterials Science 23(2012), 1185-1198.

Yan et al.; "Silk fibroin/chondroitin sulfate/hyaluronic acid Ternary scaffolds for dermal tissue receonstruction"; Acta Biomaterialia; Feb. 16, 2013.

Extended European Search Report from European Patent Application No. 13775894.2, dated Nov. 27, 2015.

Abidian MR, Martin DC. Experimental and theoretical characterization of implantable neural microelectrodes modified with conducting polymer nanotubes. Biomaterials Mar. 2008;29(9)1273-1283.

Abrams GA, Goodman SL, Nealey PF, Franco M, Murphy CJ. Nanoscale topography of the basement membrane underlying the corneal epithelium of the rhesus macaque. Cell Tissue Res Jan. 2000;299(1):39-46.

Ahmed I, Liu HY, Mamiya PC, Ponery AS, Babu AN, Weik T, et al. Three-dimensional nanofibrillar surfaces covalently modified with tenascin-C-derived peptides enhance neuronal growth in vitro. J Biomed Mater Res A Mar. 15, 2006;76(4):851-860.

Al-Majed AA, Neumann CM, Brushart TM, Gordon T. Brief electrical stimulation promotes the speed and accuracy of motor axonal regeneration. J Neurosci Apr. 1, 2000;20(7):2602-2608.

Al-Majed AA, Tam SL, Gordon T. Electrical stimulation accelerates and enhances expression of regeneration-associated genes in regenerating rat femoral motoneurons. Cell Mol Neurobiol Jun. 2004;24(3):379-402.

Batchelor PE, Porritt MJ, Martinello P, Parish CL, Liberatore GT, Donnan GA, et al. Macrophages and Microglia Produce Local Trophic Gradients That Stimulate Axonal Sprouting Toward but Not beyond the Wound Edge. Mol Cell Neurosci Nov. 2002;21(3):436-453.

(56) References Cited

OTHER PUBLICATIONS

Barrett, DG and Yousaf, MN. Design and Applications of Biodegradable Polyester Tissue Scaffolds Based on Endogenous Monomers Found in Human Metabolism. Molecules, Oct. 12, 2009.
Barras FM, Pasche P, Bouche N, Aebischer P, Zurn AD. Glial cell line-derived neurotrophic factor released by synthetic guidance channels promotes facial nerve regeneration in the rat. J Neurosci Res Dec. 15, 2002;70(6):746-755.
AshaRani PV, Hande MP, Valiyaveettil S. Anti-proliferative activity of silver nanoparticles. BMC Cell Biol Sep. 2009;10:14.
Alkilany AM, Nagaria PK, Hexel CR, Shaw TJ, Murphy CJ, Wyatt MD. Cellular Uptake and Cytotoxicity of Gold Nanorods: Molecular Origin of Cytotoxicity and Surface Effects. Small Mar. 2009;5(6):701-708.
Apte, S. S. (2011). "Current developments in the tissue engineering of autologous heart valves: moving towards clinical use." Future cardiology 7(1): 77-97.
Barakat, N.A.M., et al., "Polymeric nanofibers containing solid nanoparticles prepared by electrospinning and their applications," Chemical Engineering Journal 156:487-495 (2010).
Baron-Van Evercooren A, Kleinman HK, Ohno S, Marangos P, Schwartz JP, Dubois-Dalcq ME. Nerve growth factor laminin and fibronective promote neurite growth in human fetal sensory ganglia cultures. Journal of Neuroscience Research 1982;8(2-3):179-194.
Bondar, B., S. Fuchs, et al. (2008). "Functionality of endothelial cells on silk fibroin nets: Comparative study of micro- and nanometric fibre size." Biomaterials 29(5): 561-572.
Billiar, K. L. and M. S. Sacks (2000). "Biaxial Mechanical Properties of the Native and Glutaraldehyde-Treated Aortic Valve Cusp: Part II—A Structural Constitutive Model." Journal of Biomechanical Engineering 122(4): 327-335.
Carlson C, Hussain SM, Schrand AM, Braydich-Stolle LK, Hess KL, Jones RL, et al. Unique Cellular Interaction of Silver Nanoparticles: Size-Dependent Generation of Reactive Oxygen Species. J Phys Chem B 2008;112(43):13608-13619.
Butcher, J. T., G. J. Mahler, et al. (2011). "Aortic valve disease and treatment: The need for naturally engineered solutions." Advanced Drug Delivery Reviews 63(4-5): 242-268.
Brushart, T.M., Jari, R., Verge, V., Rohde, C. & Gordon, T. Electrical stimulation restores the specificity of sensory axon regeneration. Experimental Neurology 194, 221-229 (2005).
Boland, E.D., et al., "Electrospinning polydioxanone for biomedical applications," Acta Biomaterialia 1:115-123 (2005).
Bouquet C, Ravaille-Veron M, Propst F, Nothias F. MAP1B coordinates microtubule and actin filament remodeling in adult mouse Schwann cell tips and DRG neuron growth cones. Mol Cell Neurosci Oct. 2007;36(2):235-247.
Chen, W.-Q., H. Priewalder, et al. (2010). "Silk cocoon of Bombyx mori: Proteins and posttranslational modifications—heavy phosphorylation and evidence for lysine-mediated cross links." Proteomics 10(3): 369-379.
Chang CJ, Hsu SH, Yen HJ, Chang H, Hsu SK. Effects of unidirectional permeability in asymmetric poly(DL-lactic acid-co-glycolic acid) conduits on peripheral nerve regeneration: An in vitro and in vivo study. J Biomed Mater Res Part B Oct. 2007;83B(1):206-215.
Chen, Y., et al., "Increased osteoblast functions in the presence of BMP-7 short peptides for nanostructured biomaterial applications," J. Biomed. Mater. Res. A 91:296-304 (2009; published online Nov. 3, 2008).
Breuer, C. K. (2004). "Application of tissue-engineering principles toward the development of a semilunar heart valve substitute." Tissue engineering 10(11-12): 1725-1736.
Bruder JM, Lee AP, Hoffman-Kim D. Biomimetic materials replicating Schwann cell topography enhance neuronal adhesion and neurite alignment in vitro. J Biomater Sci Polym Ed 2007;18(8):967-982.
Bryan DJ, Holway AH, Wang KK, Silva AE, Trantolo DJ, Wise D, et al. Influence of glial growth factor and Schwann cells in a bioresorbable guidance channel on peripheral nerve regeneration. Tissue Eng Apr. 2000;6(2):129-138.
Chobanian, A. V., G. L. Bakris, et al. (2003). "Seventh Report of the Joint National Committee on Prevention, Detection, Evaluation, and Treatment of High Blood Pressure." Hypertension 42(6): 1206-1252.
Cho Y, Shi R, Ivanisevic A, Ben Borgens R. A mesoporous silica nanosphere-based drug delivery system using an electrically conducting polymer. Nanotechnology Jul. 8, 2009;20(27):275102.
Borschel GH, Kia KF, Kuzon WM, Jr., Dennis RG. Mechanical properties of acellular peripheral nerve. J Surg Res Oct. 2003;114(2):133-139.
Boyd JG, Gordon T. A dose-dependent facilitation and inhibition of peripheral nerve regeneration by brain-derived neurotrophic factor. Eur J Neurosci Feb. 2002;15(4):613-626.
Causa, F., et al., "A multi-functional scaffold for tissue regeneration: The need to engineer a tissue analogue," Biomaterials, 28(34):5093-5099 (Dec. 2007; available online Aug. 6, 2007).
Cebotari, S. (2011). "Use of fresh decellularized allografts for pulmonary valve replacement may reduce the reoperation rate in children and young adults: early report." Circulation (New York, N.Y.) 124(11 suppl): S115-123.
Chamberlain LJ, Yannas IV, Hsu HP, Strichartz GR, Sepctor M. Near-terminus axonal structure and function following rat sciatic nerve regeneration through a collagen-GAG matrix in a ten-millimeter gap. J Neurosci Res Jun. 1, 2000;610(5):666-677.
Chen, D., et al., "Application of electrostatic spinning technology in nano-structured polymer scaffold," Zhongguo Xiu Fu Chong Jian Wai Ke Za Zhi, 21(4):411-415 (Apr. 2007), 1 sheet abstract.
Chen, R., et al., "Preparation and characterization of coaxial electrospun thermoplastic polyurethane/collagen compound nanofibers for tissue engineering applications," Colloids and Surfaces B: Biointerfaces 79(2):315-325 (Sep. 1, 2010) (available online Apr. 3, 2010).
Chen YS, Hsieh CL, Tsai CC, Chen TH, Cheng WC, Hu CL, et al. Peripheral nerve regeneration using silicone rubber chambers filled with collagen, laminin and fibronectin. Biomaterials Aug. 2000;21(15):1541-1547.
Cheng C, Webber CA, Wang J, Xu Y, Martinez JA, Liu WQ, et al. Activated RHOA and peripheral axon regeneration. Exp Neurol Aug. 2008;212(2):358-369.
De S, Higgins TM, Lyons PE, Doherty EM, Nirmalraj PN, Blau WJ, et al. Silver Nanowire Networks as Flexible, Transparent, Conducting Films: Extremely High DC to Optical Conductivity Ratios. ACS Nano Jul. 2009;3(7):1767-1774.
Evans, G.R.D. et al. In vivo evaluation of poly(-lactic acid) porous conduits for peripheral nerve regeneration. Biomaterials 20, 1109-1115 (1999).
Elias, K.L., Price, R.L. & Webster, T.J. Enhanced functions of osteoblasts on nanometer diameter carbon fibers. Biomaterials 23, 3279-3287 (2002).
Dumitriu, Severian and Popa, Valentin. Polymeric Biomaterials: Structure and Function, vol. 1. Boca Raton, FL: CRC Press, Jan. 17, 2013.
Ciardelli G, Rechichi A, Cerrai P, Tricoli M, Barbani N, Giusti P. Segmented polyurethanes for medical applications: Synthesis, characterization and in vitro enzymatic degradation studies. Macromolecular Symposia 2004;218:261-271.
Deister C, Schmidt CE. Optimizing neurotrophic factor combinations for neurite outgrowth. J Neural Eng Jun. 2006;3(2):172-179.
Ekaputra, A.K., et al., "Composite electrospun scaffolds for engineering tubular bone grafts," Tissue Eng. Part A 15(12):3779-3788 (Dec. 8, 2009) (published online Jul. 20, 2009; online ahead of print: Jul. 24, 2009; online ahead of editing: Jun. 15, 2009).
Corey JM, Lin DY, Mycek KB, Chen Q, Samuel S, Feldman EL, et al. Aligned electrospun nanofibers specify the direction of dorsal root ganglia neurite growth. J Biomed Mater Res A Dec. 1, 2007;83(3):636-645.
De Cock, L. J. (2010). "Layer-by-layer incorporation of growth factors in decellularized aortic heart valve leaflets." Biomacromolecules 11(4): 1002-1008.

(56) References Cited

OTHER PUBLICATIONS

Cullen DK, A RP, Doorish JF, Smith DH, Pfister BJ. Developing a tissue-engineered neural-electrical relay using encapsulated neuronal constructs on conducting polymer fibers. J Neural Eng Dec. 2008;5(40):374-384.
Cui X, Lee VA, Raphael Y, Wiler JA, Hetke JF, Anderson DJ, et al. Surface modification of neural recording electrodes with conducting polymer/biomolecule blends. J Biomed Mater Res Aug. 2001;56(2):261-272.
Evans PJ, Bain JR, Mackinnon SE, Makino AP, Hunter DA. Selective reinnervation: a comparison of recovery following microsuture and conduit nerve repair. Brain Res Sep. 20, 1991;559(2):315-321.
Evans AJ, Thompson BC, Wallace GG, Millard R, O'Leary SJ, Clark GM, et al. Promoting neurite outgrowth from spiral ganglion neuron explants using polypyrrole/BDNF-coated electrodes. J Biomed Mater Res A Oct. 2009;91(1):241-250.
Edwards SL, Church JS, Werkmeister JA, Ramshaw JAM. Tubular micro-scale multiwalled carbon nanotube-based scaffolds for tissue engineering. Biomaterials Mar. 2009;30(9)1725-1731.
Evans GRD, Brandt K, Katz S, Chauvin P, Otto L, Bogle M, et al. Bioactive poly(L-lactic acid) conduits seeded with Schwann cells for peripheral nerve regeneration. Biomaterials Feb. 2002;23(3):841-848.
Evans GRD. Peripheral nerve injury: A review and approach to tissue engineered constructs. Anatomical Record 2001; 263(4):396-404.
Deng, M., et al., "Miscibility and in vitro osteocompatibility of biodegradable blends of poly[(ethyl alanato) (p-phenyl phenoxy) phosphazene] and poly(lacitic acid-glycolic acid)," Biomaterials 29:337-349 (2008; available online Oct. 17, 2007).
Bauhofer W, Kovacs JZ. A review and analysis of electrical percolation in carbon nanotube polymer composites. Composites Science and Technology 2009;69(10):1486-1498.
Bain JR, Mackinnon SE, Hunter DA. Functional evaluation of complete sciatic, peroneal, and posterior tibial nerve lesions in the rat. Plast Reconstr Surg Jan. 1989;83(1):129-138.
Beachley, V., et al., "Polymer nanofibrous structures: Fabrication, biofunctionalization, and cell interactions," Progress in Polymer Science, 35(7):868-892 (Jul. 2010) (available online Mar. 17, 2010).
Beun, L. H., X. J. Beaudoux, et al. (2011). "Self-Assembly of Silk-Collagen-like Triblock Copolymers Resembles a Supramolecular Living Polymerization." ACS Nano 6(1):133-140.
Boissard, C.I.R., et al., "Nanohydroxyapatite/poly(ester urethane) scaffold for bone tissue engineering," Acta Biomaterialia 5:3316-3327 (Nov. 2009; available online May 12, 2009).
Borgens RB, Vanable JW, Jr. Jaffe LF. Bioelectricity and regeneration: large currents leave the stumps of regenerating newt limbs. Proc Natl Acad Sci U S A Oct. 1977;74(10):4528-4532.
Caswell KK, Bender CM, Murphy CJ. Seedless, surfactantless wet chemical synthesis of silver nanowires. Nano Lett May 2003;3(5):667-669.
Chamberlain LJ, Yannas IV, Hsu HP, Strichartz GR, Spector M. Near-terminus axonal structure and function following rat sciatic nerve regeneration through a collagen-GAG matrix in a ten-millimeter gap. J Neurosci Res Jun. 1, 2000;60(5):666-677.
Chen X, Schluesener HJ. Nanosilver: A nanoproduct in medical application. Toxicol Lett Jan. 2008;176(1):1-12.
Chronakis, I.S., "Novel nanocomposites and nanoceramics based on polymer nanofibers using electrospinning process—A review," Journal of Materials Processing Technology 167:283-293 (2005).
Al Majed, A.A., Tam, S.L. & Gordon, T. Electrical stimulation accelerates and enhances expression of regeneration-associated genes in regenerating rat femoral motoneurons. Cellular and Molecular Neurobiology 24, 379-402 (2004).
Bashar SA. Study of Indium Tin Oxide (ITO) for Novel Optoelectronic Devices. King's College London: University of London; 1998.
Batchelor PE, Wills TE, Hewa AP, Porritt MJ, Howells DW. Stimulation of axonal sprouting by trophic factors immobilized within the wound core. Brain Res May 13, 2008;1209:49-56.

Cheng H, Hoffer B, Stromberg I, Russell D, Olson L. The effect of glial-cell line-derived neurotrophic factor in fibrin glue on developing dopamine neurons. Exp Brain Res May 1995;104(2):199-206.
Dijkman, P. E., A. Driessen-Mol, et al. (2012). "Decellularized homologous tissue-engineered heart valves as off-the-shelf alternatives to xeno- and homografts." Biomaterials 18:4545-54.
Dertinger SK, Jiang X, Li Z , Murphy VN, Whitesides GM. Gradients of substrate-bound laminin orient axonal specification of neurons. Proc Natl Acad Sci U S A Oct. 1, 2002;99(20):12542-12547.
Chiang M, Robinson KR, Vanable JW, Jr. Electrical fields in the vicinity of epithelial wounds in the isolated bovine eye. Exp Eye Res Jun. 1992;54(6):999-1003.
De Cupere, V. M., J. Van Wetter, et al. (2003). "Nanoscale Organization of Collagen and Mixed Collagen—Pluronic Adsorbed Layers." Langmuir 19(17): 6957-6967.
Deng, C. (2011). "Application of decellularized scaffold combined with loaded nanoparticles for heart valve tissue engineering in vitro." Journal of Huazhong University of Science and Technology. Medical sciences 31(1): 88-93.
FitzGerald MJT. Neuroanatomy: Basic and Clinical. Philadelphia: W.B. Saunders Company, Ltd., 1996.
Fujihara, K., et al., "Guided bone regeneration membrane made of polycaprolactone/calcium carbonate composite nano-fibers," Biomaterials 26:4139-4147 (2005; available online Dec. 24, 2004).
Deka, H., et al., "Biocompatible hyperbranched polyurethane/multi-walled carbon nanotube composites as shape memory materials," Carbon 48:2013-2022 (2010; available online Feb. 11, 2010).
Franzen R, Tanner SL, Dashiell SM, Rottkamp CA, Hammer JA, Quarles RH. Microtubule-associated protein 1B: a neuronal binding partner for myelin-associated glycoprotein. J Cell Biol Dec. 10, 2001;155(6):893-898.
Gerecht S, Townsend SA, Pressler H, Zhu H, Nijst CLE, Bruggeman JP, et al. A porous photocurable elastomer for cell encapsulation and culture. Biomaterials Nov. 2007;28(32):4826-4835.
Gallo G. RhoA-kinase coordinates F-actin organization and myosin II activity during semaphoring-3A-induced axon retraction. J Cell Sci Aug. 15, 2006;119(Pt 16):3413-3423.
Goold RG, Gordon-Weeks PR. Glycogen synthase kinase 3beta and the regulation of axon growth. Biochem Soc Trans Nov. 2004;32(Pt 5):809-811.
Goldner JS, Bruder JM, Li G, Gazzola D, Hoffman-Kim D. Neurite bridging across micropatterned grooves. Biomaterials Jan. 2006;27(3):460-472.
Dohmen, P. M., A. Lembcke, et al. (2011). "Ten Years of Clinical Results With a Tissue-Engineered Pulmonary Valve." The Annals of Thoracic Surgery 92(4): 1308-1314.
Goold RG, Gordon-Weeks PR. NGF activates the phosphorylation of MAP1B by GSK3beta through the TrkA receptor and not the p75(NTR) receptor. J Neurochem Nov. 2003;87(4):935-946.
Gordon T. The role of neurotrophic factors in nerve regeneration. Neurosurg Focus 2009;26(2):E3.
Gole A, Murphy CJ. Seed-mediated synthesis of gold nanorods: Role of the size and nature of the seed. Chem Mat Sep. 2004;16(19):3633-3640.
Gonzalez-Billault C, Jimenez-Mateos EM, Caceres A, Diaz-Nido J, Wandosell F, Avila J. Microtube-associated protein 1B function during normal development, regeneration, and pathological conditions in the nervous system. J Neurobiol Jan. 2004;58(1):48-59.
Dong, B., et al., "Electrospinning of collagen nanofiber scaffolds from benign solvents," Macromolecular Rapid Communications 30(7):539-542 (Feb. 5, 2009).
Faria, M.L.E., et al., "Recombinant human bone morphogenetic protein-2 in absorbable collagen sponge enhances bone healing of tibial osteotomies in dogs," Veterinary Surgery 36(2):122-131 (Feb. 2007; first published online Mar. 2, 2007).
Garcia-Perez J, Avila J, Diaz-Nido J. Implication of cyclin-dependent kinases and glycogen synthase kinase 2 in the phosphorylation of microtubule-associated protein 1B in developing neuronal cells. J Neurosci Res May 15, 1998;52(4):445-452.

(56) References Cited

OTHER PUBLICATIONS

George PM, Lyckman AW, LaVan DA, Hegde A, Leung Y, Avasare R, et al. Fabrication and biocompatibility of polypyrrole implants suitable for neural prosthetics. Biomaterials Jun. 2005;26(17):3511-3519.
Goold RG, Gordon-Weeks PR. The MAP kinase pathway is upstream of the activation of GSK3beta that enables it to phosphorylate MAP1B and contributes to the stimulation of axon growth. Mol Cell Neurosci Mar. 2005;28(3):524-534.
Guan J, Stankus JJ, Wagner WR. Biodegradable elastomeric scaffolds with basic fibroblast growth factor release. Journal of Controlled Release 2007;120(1-2):70-78.
Gu, X. And K. S. Masters (2010). "Regulation of valvular interstitial cell calcification by adhesive peptide sequences." Journal of Biomedical Materials Research Part A 93A(4):1620-1630.
Hayashi, T. and S. Mukamel (2007). "Vibrational-Exciton Couplings for the Amide I, II, III, and A Modes of Peptides." The Journal of Physical Chemistry B 111(37):11032-11046.
Hayashi A, Moradzadeh A, Tong A, Wei C, Tuffaha SH, Hunter DA, et al. Treatment modality affects allograft-derived Schwann cell phenotype and myelinating capacity. Exp Neurol Aug. 2008;212(2):324-336.
Hopkins, R. A. (2005). "Tissue engineering of heart valves: decellularized valve scaffolds." Circulation (New York, N.Y.) 111(21): 2712-2714.
Guimard NK, Gomez N, Schmidt CE. Conducting polymers in biomedical engineering. Progress in Polymer Science 2007;32:876-921.
Hinton, R. B. and K. E. Yutzey (2011). "Heart Valve Structure and Function in Development and Disease." Annual Review of Physiology 73(1): 29-46.
Hill, C.A., et al., "Superior sternal cleft repair using autologous rib grafts in an infant with complex congenital heart disease," Ann. Thorac. Surg., 84:673-4, (2007).
Horan, R. L., K. Antle, et al. (2005). "In vitro degradation of silk fibroin." Biomaterials 26(17): 3385-3393.
Hoshi, R.A., "Nanoporous biodegradable elastomers," Adv. Mater. 21:188-192 (2009).
Ifkovits JL, Devlin JJ, Eng G, Martens TP, Vunjak-Novakovic G, Burdick JA. Biodegradable Fibrous Scaffolds with Tunable Properties Formed from Photo-Cross-Linkable Poly(glycerol sebacate). ACS Appl Mater Interfaces Sep. 2009;1(9):1878-1886.
Hu, H. et al. Polyethyleneimine functionalized single-walled carbon nanotubes as a substrate for neuronal growth. Journal of Physical Chemistry B 109, 4285-4289 (2005).
International Preliminary Report on Patentability from International Application No. PCT/US2013/032520 dated Oct. 14, 2014.
Integra. NeuraWrap Nerve Protector. 2009; Available from: http://www.integra-ls.com/products/?product=198.
Integra. NeuraGen Nerve Guide. 2009; Available from: http://www.integra-ls.com/products/?product=88.
International Preliminary Report on Patentability from International Application No. PCT/US2013/066747, dated Apr. 28, 2015.
Hong, Y., et al., "Tailoring the degradation kinetics of poly(ester carbonate urethane)urea thermoplastic elastomers for tissue engineering scaffolds," Biomaterials 31:4249-4258 (2010; available online Feb. 25, 2010).
Jain, A., Kim, Y.T., Mckeon, R.J. & Bellamkonda, R.V. In situ gelling hydrogels for conformal repair of spinal cord defects, and local delivery of BDNF after spinal cord injury. Biomaterials 27, 497-504 (2006).
Hu, X., D. Kaplan, et al. (2006). "Determining Beta-Sheet Crystallinity in Fibrous Proteins by Thermal Analysis and Infrared Spectroscopy." Macromolecules 39(18): 6161-6170.
Hu H, Ni YC, Montana V, Haddon RC, Parpura V. Chemically functionalized carbon nanotubes as substrates for neuronal growth. Nano Lett 2004;4(3):507-511.
Huang J, Hu X, Lu L, Ye Z, Zhang Q, Luo Z. Electrical regulation of Schwann cells using conductive polypyrrole/chitosan polymers. J Biomed Mater Res A Jun. 17, 2009.

Hudson TW, Evans GR, Schmidt CE. Engineering strategies for peripheral nerve repair. Orthop Clin North Am Jul. 2000;31(3):485-498.
Medscape: Diseases of the Peripheral Nervous System. Web MD Inc., ACP Medicine, 2004.
Song YX, Muramatsu K, Kurokawa Y, Kuriyama R, Sakamoto S, Kaneko K, et al. Functional recovery of rat hind-limb allografts. J Reconstr Microsurg Oct. 2005;21(7):471-476.
Luis AL, Rodrigues JM, Lobato JV, Lopes MA, Amado S, Veloso AP, et al. Evaluation of two biodegradable nerve guides for the reconstruction of the rat sciatic nerve. Biomed Mater Eng 2007;17(1):39-52.
Pigino G, Paglini G, Ulloa L, Avila J, Caceres A. Analysis of the expression, distribution and function of cyclin dependent kinase 5 (cdk5) in developing cerebellar macroneurons. J Cell Sci Jan. 1997;110 (Pt 2):257-270.
Riederer BM, Moya F, Calvert R. Phosphorylated MAP1b, alias MAP5 and MAP1x, is involved in axonal growth and neuronal mitosis. Neuroreport Jun. 1993;4(6):771-774.
Stoll G, Muller HW. Nerve injury, axonal degeneration and neural regeneration: basic insights. Brain Pathol Apr. 1999;9(2):313-325.
Loudon RP, Silver LD, Yee HF, Jr., Gallo G. RhoA-kinase and myosin II are required for the maintenance of growth cone polarity and guidance by nerve growth factor. J Neurobiol Jul. 2006;66(8):847-867.
Melendez-Vasquez CV, Einheber S, Salzer JL. Rho kinase regulates Schwann cell myelination and formation of associated axonal domains. J Neurosci Apr. 21, 2004;24(16):3953-3963.
Sherman DL, Brophy PJ. Mechanisms of axon ensheathment and myelin growth. Nat Rev Neurosci Sep. 2005;6(9):683-690.
Sharma N, Marzo SJ, Jones KJ, Foecking EM. Electrical stimulation and testosterone differentially enhance expression of regeneration-associated genes. Exp Neurol May 7, 2009.
Tsujino H, Kondo E, Fukuoka T, Dai Y, Tokunaga A, Miki K, et al. Activating transcription factor 3 (ATF3) induction by axotomy in sensory and motoneurons: A novel neuronal marker of nerve injury. Mol Cell Neurosci Feb. 2000;15(2):170-182.
Geremia NM, Gordon T, Brushart TM, Al-Majed AA, Verge VM. Electrical stimulation promotes sensory neuron regeneration and growth-associated gene expression. Exp Neurol Jun. 2007;205(2):347-359.
McIntyre CC, Richardson AG, Grill WM. Modeling the excitability of mammalian nerve fibers: influence of afterpotentials on the recovery cycle. J Neurophysiol Feb. 2002;87(2):995-1006.
Shanthaveerappa TR, Bourne H. Histological and histochemical studies of the choroid of the eye and its relations to the pia-arachnoid mater of the central nervous system and perineural epithelium of the peripheral nervous system. Acta Anat (Basel) 1965;61(3):379-398.
Jana NR, Gearheart L, Murphy CJ. Wet chemical synthesis of high aspect ratio cylindrical gold nanorods. J Phys Chem B May 2001;105(19):4065-4067.
Johnson EO, Soucacos PN. Nerve repair: experimental and clinical evaluation of biodegradable artificial nerve guides. Injury Sep. 2008;39 Suppl 3:S30-36.
Wang S, Yaszemski MJ, Knight AM, Gruetzmacher JA, Currier BL, Yaszemski MJ. Synthesis and characterizations of biodegradable and crosslinkable poly(epsilon-caprolactone fumarate), poly(ethylene glycol fumarate), and their amphiphilic copolymer. Biomaterials Feb. 2006;27(6):832-841.
Wang S, Yaszemski MJ, Knight AM, Gruetzmacher JA, Windebank AJ, Lu L. Photo-crosslinked poly(epsilon-caprolactone fumarate) networks for guided peripheral nerve regeneration: material properties and preliminary biological evaluations. Acta Biomater Jun. 2009:5(5):1 531-1542.
Hadlock T, Sundback C, Hunter D, Cheney M, Vacanti JP. A polymer foam conduit seeded with Schwann cells promotes guided peripheral nerve regeneration. Tissue Engineering 2000;6(20):119-127.
Hollowell JP, Villadiego A, Rich KM. Sciatic nerve regeneration across gaps within silicone chambers: long-term effects of NGF and consideration of axonal branching. Exp Neurol Oct. 1990;110(1):45-51.

(56) References Cited

OTHER PUBLICATIONS

Wood MD, Moore AM, Hunter DA, Tuffaha S, Borschel GH, Mackinnon SE, et al. Affinity-based release of glial-derived neurotrophic factor from fibrin matrices enhances sciatic nerve regeneration. Acta Biomater May 2009;5(4):959-968.

Lietz M, Dreesmann L, Hoss M, Oberhoffner S, Schlosshauer B. Neuro tissue engineering of glial nerve guides and the impact of different cell types. Biomaterials Mar. 2006;27(8):1425-1436.

Song J, Cheng Q, Kopta S, Stevens RC. Modulating artificial membrane morphology: pH-induced chromatic transition and nanostructural transformation of a bolaamphiphilic conjugated polymer from blue helical ribbons to red nanofibers. J Am Chem Soc Apr. 11, 2001;123(14):3205-3213.

Kehoe S, Zhang XF, Boyd D. FDA approved guidance conduits and wraps for peripheral nerve injury: A review of materials and efficacy. Injury-Int J Care Inj May;43(5):553-572.

Pomerantseva I, Krebs N, Hart A, Neville CM, Huang AY, Sundback CA. Degradation behavior of poly(glycerol sebacate). J Biomed Mater Res Part A Dec. 2009;91A(4):1038-1047.

Wang YD, Ameer GA, Sheppard BJ, Langer R. A tough biodegradable elastomer. Nature Biotechnology Jun. 2002;20(6):602-606.

Nijst CLE, Bruggeman JP, Karp JM, Ferreira L, Zumbuehl A, Bettinger CJ, et al. Synthesis and characterization of photocurable elastomers from poly(glycerol-co-sebacate). Biomacromolecules Oct. 2007;8(10):3067-3073.

Svennersten K, Bolin MH, Jager EWH, Berggren M, Richter-Dahlfors A. Electrochemical modulation of epithelia formation using conducting polymers. Biomaterials Nov. 2009;30(31):6257-6264.

Luo XL, Weaver CL, Zhou DD, Greenberg R, Cui XYT. Highly stable carbon nanotube doped poly(3,4-ethylenedioxythiophene) for chronic neural stimulation. Biomaterials Aug;32(24):5551-5557.

Shi GX, Rouabhia M, Wang ZX, Dao LH, Zhang Z. A novel electrically conductive and biodegradable composite made of polypyrrole nanoparticles and polylactide. Biomaterials Jun. 2004; 25(13):2477-2488.

Liu QY, Tian M, Ding T, Shi R, Feng YX, Zhang LQ, et al. Preparation and characterization of a thermoplastic poly(glycerol sebacate) elastomer by two-step method. J Appl Polym Sci Feb. 2007;103(3):1412-1419.

Evans GR. Challenges to nerve regeneration. Semin Surg Oncol Oct.-Nov. 2000;19(3):312-318.

Zhang DH, Kandadai MA, Cech J, Roth S, Curran SA. Poly(L-lactide) (PLLA)/multiwalled carbon nanotube (MWCNT) composite: Characterization and biocompatibility evaluation. J Phys Chem B 2006;110(26):12910-12915.

Schense JC, Bloch J, Aebischer P, Hubbell JA. Enzymatic incorporation of bioactive peptides into fibrin matrices enhances neurite extension. Nature Biotechnology Apr. 2000;18(4):415-419.

Lee AC, Yu VM, Lowe JB, 3rd, Brenner MJ, Hunter DA, Mackinnon SE, et al. Controlled release of nerve growth factor enhances sciatic nerve regeneration. Exp Neurol Nov. 2003;184(1):295-303.

Miller C, Jeftinija S, Mallapragada S. Micropatterned Schwann cell-seeded biodegradable polymer substrates significantly enhance neurite alignment and outgrowth. Tissue Engineering Dec. 2001;7(6):705-715.

Zhao M, AgiusFernandez A, Forrester JV, McCaig CD. Orientation and directed migration of cultured corneal epithelial cells in small electric fields are serum dependent. Journal of Cell Science Jun. 1996;109:1405-1414.

Zhao M, McCaig Cd, AgiusFernandez A, Forrester JV, ArakiSasaki K. Human corneal epithelial cells reorient and migrate cathodally in a small applied electric field. Current Eye Research 1997;16(10):973-984.

Edelman ER, Mathiowitz E, Langer R, Klagsbrun M. Controlled and modulated release of basic fibroblast growth factor. Biomaterials Sep. 1991;12(7):619-626.

McDonald, D.S. & Zochodne, D.W. An injectable nerve regeneration chamber for studies of unstable soluble growth factors. Journal of Neuroscience Methods 122, 171-178 (2003).

Phillips,J.B., Bunting, S.C.J., Hall ,S.M. & Brown, R.A. Neural tissue engineering: A self-organizing collagen guidance conduit. Tissue Engineering 11, 1611-1617 (2005).

Jubran,M. & Widenfalk, J. Repair of peripheral nerve transections with fibrin sealant containing neurotrophic factors. Experimental Neurology 181, 204-212 (2003).

Foley,J.D., Grunwald, E.W., Nealey, P.F. & Murphy, C.J. Cooperative modulation of neuritogenesis by PC12 cells by topography and nerve growth factor. Biomaterials 26, 3639-3644 (2005).

Yusuka Katayama et al. Coil-Reinforced hydrogel tubes promote nerve regeneration equivalent to that of nerve autografts. Biomaterials 27, 503-518 (2006).

Yuan, Y., Zhang, P., Yang, Y., Wang, X. & Gu, X. The interaction of Schwann cells with chitosan membranes and fibers in vitro. Biomaterials 25, 4273-4278 (2004).

Lietz, M. et al. Physical and biological performance of a novel block copolymer nerve guide. Biotechnology and Bioengineering 93, 99-109 (2006).

Keilhoff,G., Stang, F., Wolf, G. & Fansa, H. Bio-compatibility of type I/III collagen matrix for peripheral nerve reconstruction. Biomaterials 24, 2779-2787 (2003).

Li, M., Guo, Y., Wei, Y., MacDiarmid, A.G. & Lelkes, P.I. Electrospinning polyaniline-contained gelatin nanofibers for tissue engineering applications. Biomaterials 27, 2705-2715 (2006).

Novikova,L.N. et al. Alginate hydrogel and matrigel as potential cell carriers for neurotransplantation. Journal of Biomedical Materials Research Part A 77A, 242-252 (2006).

Ming, G.I., Henley, J., Tessier-Lavigne, M., Song, H.J. & Poo, M.m. Electrical Activity Modulates Growth Cone Guidance by Diffusible Factors. Neuron 29, 441-452 (2001).

Terell Rivers, Terry Hudson & Christine Schmidt. Synthesis of a Novel, Biodegradable Electrically Conducting Polymer for Biomedical Applications. Advanced Functional Materials 12, 33-37 (2002).

Kotwal, A. & Schmidt, C.E. Electrical stimulation alters protein adsorption and nerve cell interactions with electrically conducting biomaterials. Biomaterials 22, 1055-1064 (2001).

Yang, L., Feng, J.K. & Ren, A.M. Structural, electronic and optical properties of a series of oligofluorene-thiophene oligomers and polymers. Journal of Molecular Structure-Theochem 758, 29-39 (2006).

Suzuki, M., Fukuyama, M., Hori, Y. & Hotta, S. Electroluminescent features of oligothiophenes dispersed as a dopant in host matrices. Journal of Applied Physics 91, 5706-571 1 (2002).

Xu, H. et al. High-performance field-effect transistors based on Langmuir-Blodgett films of cyclo[8]pyrrole. Langmuir 21, 5391-5395 (2005).

Zhang L, Ma Z, Smith GM, Wen X, Pressman Y, Wood PM, et al. GDNF-enhanced axonal regeneration and myelination following spinal cord injury is mediated by primary effects on neurons. Glia Jan. 23, 2009.

Jin, Z., Pramoda, K.P., Xu, G. & Goh, S.H. Dynamic mechanical behavior of meltprocessed multi-walled carbon nanotubelpoly(methyl methacrylate) composites. Chemical Physics Letters 337, 43-47 (2001).

Webster, T.J., Waid, M.C., McKenzie, J.L., Price, R.L. & Ejiofor, J.U. Nanobiotechnology: carbon nanofibres as improved neural and orthopaedic implants. Nanotechnology 15, 48-54 (2004).

Wei, G. et al. One-step synthesis of silver nanoparticles, nanorods, and nanowires on the surface of DNA network. Journal of Physical Chemistry B 109, 8738-8743 (2005).

Murphy, C.J., Gole, A.M., Hunyadi, S.E. & Orendorff, C.J. One-dimensional colloidal gold and silver nanostructures. Inorganic Chemistry 45,7544-7554 (2006).

Orendorff, C.J., Gearheart, L., Jana, N.R. & Murphy, C.J. Aspect ratio dependence on surface enhanced Raman scattering using silver and gold nanorod substrates. Physical Chemistry Chemical Physics 8, 165-170 (2006).

Min, B.M., You, Y., Kim, J.M., Lee, S.J. & Park, W.H. Formation of nanostructured poly(lactic-co-glycolic acid)/chitin matrix and its cellular response to normal human keratinocytes and fibroblasts. Carbohydrate Polymers 57, 285-292 (2004).

(56) References Cited

OTHER PUBLICATIONS

Mattson, M.P., Haddon, R.C. & Rao, A.M. Molecular functionalization of carbon nanotubes and use as substrates for neuronal growth. Journal of Molecular Neuroscience 14, 175-182 (2000).
Ni, Y.C. et al. Chemically functionalized water soluble single-walled carbon nanotubes modulate neurite outgrowth. Journal of Nanoscience and Nanotechnology 5, 1707-171 2 (2005).
Zhang X, MacDiarmid AG, Manohar SK. Chemical synthesis of PEDOT nanofibers. Chem Commun (Camb) Nov. 14, 2005(42):5328-5330.
Lansdown, A.B.G. Critical observations on the neurotoxicity of silver. Critical Reviews in Toxicology 37, 237-250 (2007).
Schmidt, C.E. Ann Rev Biomed Engr 5:293-347 (2003).
Rosenbalm, T., Levi-Polyachenko, N., and Wagner, W.D. Development of repeated biphasic conducting materials for peripheral nerve repair. Gordon Conference on Biochemistry, The Complex Membrane of the Electric Field, University of New England, Biddeford, ME (Jul. 11-16, 2010).
Oh, et al. High molecular weight soluble polypyrrole. Synthetic Metals 125: 267-272 (2002).
Taunk, M. et al. Hopping and tunneling transport over a wide temperature range in chemically synthesized doped and undoped polypyrrole. Solid State Communications 150: 1766-1769 (2010).
Yen, S-J et al. Preparation and characterization of polypyrrole/magnetite nanocomposites synthesized by in situ chemical oxidative polymerization. Journal of Polymer Sciences B: Polymer Physics 46: 1291-1300 (2008).
Lu, X. et al. Preparation and characterization of conducting polycaprolactone/chitosan/polypyrrole composites. Composites: Part A. 41: 1516-1523 (2010).
Oh, S.H. et al. Peripheral nerve regeneration within an asymmetrically porous PLGA/Pluronic F127 nerve guide conduit. Biomaterials 29: 1601-1609 (2008).
Oh, E.J. et al. Synthesis and characterization of high molecular weight, highly soluble polypyrrole in organic solvents. Synthetic Metals 119: 109-110 (2001).
Shi, G. et al. A novel electrically conductive and biodegradable composite made of polypyrrole nanoparticles and polylactide. Biomaterials 25: 2477-2488 (2004).
Meek MF, Coert JH. US Food and Drug Administration/Conformit Europe-approved absorbable nerve conduits for clinical repair of peripheral and cranial nerves. Ann Plast Surg Jan. 2008;60(1):110-116.
Kim YT, Haftel VK, Kumar S. Bellamkonda RV. The role of aligned polymer fiber-based constructs in the bridging of long peripheral nerve gaps. Biomaterials Jul. 2008;29(21):3117-3127.
Thomas, C.A. et al. Poly(3,4-alkylenedioxypyrrole)s as highly stable aqueous-compatible conducting polymers with biomedical implications. Adv. Mater 12: 222 (2000).
Wan, Y. et al. Porous-conductive chitosan scaffolds for tissue engineering II. In vitro and in vivo degradation. Journal of Materials Science: Materials in Medicine 16: 1017-1028 (2005).
Wan, Y. et al. Porous-Conductive Scaffolds for Tissue Engineering, 1: Preparation and Characterization. Macromol. Biosci. 4: 882-890 (2004).
Wang, Z. et al. In vivo evaluation of a novel electrically conductive polypyrrole/poly(D,L-lactide) composite and polypyrrole-coated poly(D,L-lactide-co-glycolide) membranes. J. Biomed Mater Res 70A: 28-38 (2004).
Yan, F. et al. Preparation of electrically conducting polypyrrole in oil/water microemulsion. J Appl Polym Sci 77: 135-140 (2000).
International Search Report from International Application No. PCT/US2013/032520 dated Aug. 2, 2013.
Written Opinion from International Application No. PCT/US2013/032520 dated Aug. 2, 2013.
Stryker. Stryker Neuromatrix. 2009; Available from: http://www.stryker.com/en-us/products/Trauma/PeripheralNerveRepair/NeuroMatrix/index.htm.
Kenar et al. (2010). Design of 3D aligned mycoardial tissue construct from biodegradable polyesters. J. Mater. Med 21:989-997.
Stryker. Stryker Neuroflex. 2009; Available from: http://www.stryker.com/en-us/products/Trauma/PeripheralNeryeRepair/Neuroflex/index.htm.
Polyganics. Neurolac. 2009; Available from: http://www.polyganics.nl/index.php?id=19.
Synovis Micro Companies Alliance I. GEM Neurotube. 2009; Available from: http://www.synovismicro.com/gem_neurotube.php.
SaluMedica. SaluBridge Physician Information. 2009; Available from: http://www.salumedica.com/salubridgeinfodoc.htm.
Motlagh et al. (2006) "Hemocompatibility Evaluation of Poly(glycerol-sebacate) in vitro for vascular tissue engineering", Biomaterials 27(24): 4315-4324.
Wang et al. (2012) "Novel Nanofiber-based Graft for Heart Valve Replacement," Thesis for Master of Science, Biomedical Engineering, Wake Forest University Dec. 12, 2012.
Lang et al. (2014) "A blood-resistant surgical glue for minimally invasive repair of vessels and heart defects," Science Translational Medicine, 6(218): 1-6.
Wen X, Tresco PA. Effect of filament diameter and extracellular matrix molecule precoating on neurite outgrowth and Schwann cell behavior on multifilament entubulation bridging device in vitro. J Biomed Mater Res A Mar. 1, 2006;76(3):626-637.
Cilurzo, F., C. G. M. Gennari, et al. (2011). "An investigation into silk fibroin conformation in composite materials intended for drug delivery." International Journal of Pharmaceutics 414(1-2): 218-224.
Edwards, M. B., E. R. Draper, et al. (2005). "Mechanical testing of human cardiac tissue: some implications for MRI safety." J Cardiovasc Magn Reson 7(5): 835-840.
Fan YW, Cui FZ, Chen LN, Zhai Y, Xu QY, Lee IS. Adhesion of neural cell son silicon wafer with nano-topographic surface. Applied Surface Science 2002;187(3-4):313-318.
Jiang, C., X. Wang, et al. (2007). "Mechanical Properties of Robust Ultrathin Silk Fibroin Films." Advanced Functional Materials 17(13): 2229-2237.
Jordan, J. E., J. K. Williams, et al. (2012). "Bioengineered self-seeding heart valves." The Journal of thoracic and cardiovascular surgery 143(1): 201-208.
Kidane, A. G., G. Burriesci, et al. (2009). "A novel nanocomposite polymer for development of synthetic heart valve leaflets." Acta Biomaterialia 5(7): 2409-2417.
Kim, K., M. Yu, et al. (2003). "Control of degradation rate and hydrophilicity in electrospun non-woven poly(d,l-lactide) nanofiber scaffolds for biomedical applications." Biomaterials 24(27): 4977-4985.
Lee, K.-W., D. B. Stolz, et al. (2011). "Substantial expression of mature elastin in arterial constructs." Proceedings of the National Academy of Sciences 108(7): 2705-2710.
Liu, T., W. K. Teng, et al. (2010). "Photochemical crosslinked electrospun collagen nanofibers: Synthesis, characterization and neural stem cell interactions." Journal of Biomedical Materials Research Part A 95A(1): 276-282.
Lombardi, S. J. and D. L. Kaplan (1990). "The Amino Acid Composition of Major Ampullate Gland Silk (Dragline) of Nephila Clavipes (Araneae, Tetragnathidae)." Journal of Arachnology 18(3): 297-306.
Malafaya, P. B., G. A. Silva, et al. (2007). "Natural-origin polymers as carriers and scaffolds for biomolecules and cell delivery in tissue engineering applications." Advanced Drug Delivery Reviews 59(4-5): 207-233.
Mendelboum Raviv, S., K. Szekeres-Csiki, et al. (2011). "Coating conditions matter to collagen matrix formation regarding von Willebrand factor and platelet binding." Thrombosis Research 129(4):e29-35.
Schmalenberg KE, Uhrich KE. Micropatterned polymer substrates control alignment of proliferating Schwann cells to direct neuronal regeneration. Biomaterials Apr. 2005;26(12):1423-1430.
Minoura, N., M. Tsukada, et al. (1990). "Fine structure and oxygen permeability of silk fibroin membrane treated with methanol." Polymer 31(2): 265-269.
Mirensky, T. L. and C. K. Breuer (2008). "The Development of Tissue-Engineered Grafts for Reconstructive Cardiothoracic Surgical Applications." Pediatr Res 63(5): 559-568.

(56) References Cited

OTHER PUBLICATIONS

Mol, A. (2004). "Review article: Tissue engineering of semilunar heart valves: current status and future developments." The Journal of heart valve disease 13(2): 272-280.
Newton, D., R. Mahajan, et al. (2009). "Regulation of material properties in electrospun scaffolds: Role of cross-linking and fiber tertiary structure." Acta Biomaterialia 5(1): 518-529.
Nkomo, V. T., J. M. Gardin, et al. (2006). "Burden of valvular heart diseases: a population-based study." The Lancet 368(9540): 1005-1011.
Okhawilai, M. (2010). "Preparation of Thai silk fibroin/gelatin electrospun fiber mats for controlled release applications." International journal of biological macromolecules 46(5): 544-550.
Pomerantseva, I., N. Krebs, et al. (2009). "Degradation behavior of poly(glycerol sebacate)." Journal of Biomedical Materials Research Part A 91A(4): 1038-1047.
Rockwood, D. N., R. C. Preda, et al. (2011). "Materials fabrication from Bombyx mori silk fibroin." Nat. Protocols 6(10): 1612-1631.
Ruzmetov, M., J. J. Shah, et al. (2012). "Decellularized versus standard cryopreserved valve allografts for right ventricular outflow tract reconstruction: A single-institution comparison." The Journal of thoracic and cardiovascular surgery 143(3): 543-549.
Sacks, M. S., F. J. Schoen, et al. (2009). "Bioengineering Challenges for Heart Valve Tissue Engineering." Annual Review of Biomedical Engineering 11(1): 289-313.
Sant, S., C. M. Hwang, et al. (2011). "Hybrid PGS—PCL microfibrous scaffolds with improved mechanical and biological properties." Journal of Tissue Engineering and Regenerative Medicine 5(4): 283-291.
Sant, S. and A. Khademhosseini (2010). Fabrication and characterization of tough elastomeric fibrous scaffolds for tissue engineering applications. Engineering in Medicine and Biology Society (EMBC), 2010 Annual International Conference of the IEEE.
Schopka, S. (2009). "Recellularization of biological heart valves with human vascular cells: in vitro hemocompatibility assessment." Journal of biomedical materials research. Part B, Applied biomaterials 88(1): 130-138.
Schroeder, W. A., L. M. Kay, et al. (1955). "The Amino Acid Composition of Bombyx mori Silk Fibroin and of Tussah Silk Fibroin." Journal of the American Chemical Society 77(14): 3908-3913.
Sell, S. A., M. J. McClure, et al. (2009). "Electrospinning of collagen/biopolymers for regenerative medicine and cardiovascular tissue engineering." Advanced Drug Delivery Reviews 61(12): 1007-1019.
Sell, S. A., P. S. Wolfe, et al. (2010). "The Use of Natural Polymers in Tissue Engineering: A Focus on Electrospun Extracellular Matrix Analogues." Polymers 2(4): 522-553.
Shekaran, A. and A. J. Garcia (2011). "Nanoscale engineering of extracellular matrix-mimetic bioadhesive surfaces and implants for tissue engineering." Biochimica et Biophysica Acta (BBA)—General Subjects 1810(3): 350-360.
Simon, P., M. T. Kasimir, et al. (2003). "Early failure of the tissue engineered porcine heart valve SYNERGRAFTÃ?® in pediatric patients." European Journal of Cardio-Thoracic Surgery 23(6): 1002-1006.
Simone, E. A., T. D. Dziubla, et al. (2009). "Filamentous Polymer Nanocarriers of Tunable Stiffness that Encapsulate the Therapeutic Enzyme Catalase." Biomacromolecules 10(6): 1324-1330.
Soliman, S., S. Sant, et al. (2011). "Controlling the porosity of fibrous scaffolds by modulating the fiber diameter and packing density." Journal of Biomedical Materials Research Part A 96A(3): 566-574.
Sung, H.-W., C.-N. Chen, et al. (2000). "In vitro surface characterization of a biological patch fixed with a naturally occurring crosslinking agent." Biomaterials 21(13): 1353-1362.
Tedder, M. E. (2009). "Stabilized collagen scaffolds for heart valve tissue engineering." Tissue engineering. Part A 15(6): 1257-1268.

Trowbridge, E. A., P. V. Lawford, et al. (1989). "Pericardial heterografts: a comparative study of suture pull-out and tissue strength." Journal of Biomedical Engineering 11(4): 311-314.
Um, I. C., H. Kweon, et al. (2001). "Structural characteristics and properties of the regenerated silk fibroin prepared from formic acid." International journal of biological macromolecules 29(2): 91-97.
Vesely, I. and R. Noseworthy (1992). "Micromechanics of the fibrosa and the ventricularis in aortic valve leaflets." Journal of Biomechanics 25(1): 101-113.
Wan, L.-S. and Z.-K. Xu (2009). "Polymer surfaces structured with random or aligned electrospun nanofibers to promote the adhesion of blood platelets." Journal of Biomedical Materials Research Part A 89A(1): 168-175.
Wang, Y., G. A. Ameer, et al. (2002). "A tough biodegradable elastomer." Nat Biotech 20(6): 602-606.
Yacoub, M. H. and L. H. Cohn (2004). "Novel Approaches to Cardiac Valve Repair." Circulation 109(9): 1064-1072.
Yacoub, M. H. and J. J. M. Takkenberg (2005). "Will heart valve tissue engineering change the world?" Nat Clin Pract Cardiovasc Med 2(2): 60-61.
Yamada, K. M., D. W. Kennedy, et al. (1980). "Characterization of fibronectin interactions with glycosaminoglycans and identification of active proteolytic fragments." Journal of Biological Chemistry 255(13): 6055-6063.
Rydevik BL, Kwan MK, Myers RR, Brown RA, Triggs KJ, Woo SLY, et al. An Invitro Mechanical and Histological Study of Acute Stretching on Rabbit Tibial Nerve. Journal of Orthopaedic Research 1990;8(5):694-701.
Yi, F. and D. A. LaVan (2008). "Poly(glycerol sebacate) Nanofiber Scaffolds by Core/Shell Electrospinning." Macromolecular Bioscience 8(9): 803-806.
Yoganathan, A. P., Z. He, et al. (2004). "Fluid Mechanics of Heart Valves." Annual Review of Biomedical Engineering 6(1): 331-362.
Zhou, C.-Z., et al. (2001) "Silk Fibroin: Structural implications of a remarkable amino acid sequence." Proteins: Structure, Function, and Bioinformatics 44(2): p. 119-122.
Zhou, J., C. Cao, et al. (2010). "In vitro and in vivo degradation behavior of aqueous-derived electrospun silk fibroin scaffolds." Polymer Degradation and Stability 95(9): 1679-1685.
Zhu, J., A. Negri, et al. (2010). "Closed headpiece of integrin alphaIIbbeta3 and its complex with an alphaIIbbeta3-specific antagonist that does not induce opening." Blood(Aug. 2, 2010): Dec. 2010 2012;2116(2023):5050-2019.
Zoccola, M., A. Aluigi, et al. (2008). "Study on Cast Membranes and Electrospun Nanofibers Made from Keratin/Fibroin Blends." Biomacromolecules 9(10): 2819-2825.
Zong, X., S. Ran, et al. (2003). "Structure and Morphology Changes during in Vitro Degradation of Electrospun Poly(glycolide-co-lactide) Nanofiber Membrane." Biomacromolecules 4(2): 416-423.
Zou, L., S. Cao, et al. (2012). "Fibronectin induces endothelial cell migration through beta1-integrin and Src dependent phosphorylation of fibroblast growth factor receptor-1 at tyrosines 653/654 and 766." Journal of Biological Chemistry.
Nair et al. (2004). "Development of novel tissue engineering scaffolds via electrospinning." Exper. Opin. Biol. Ther. 4:659-668.
Van Susante, J.L.C., et al., "Linkage of chondroitin-sulfate to type I collagen scaffolds stimulates the bioactivity of seeded chondrocytes in vitro," Biomaterials, 22:2359-2369 (2001).
Sasaki, N., et al., "Stress-strain curve and Young's Modulus of a collagen molecule as determined by the x-ray diffraction technique," J. Biomechanics, 29(5):655-658 (1996).
Nagata, M., et al., "Synthesis, characterization, and enzymatic degradation of network aliphatic copolyesters," Journal of Polymer Science: Part A: Polymer Chemistry, 37:2005-2011 (1999).
Webb, A.R., et al., "Biodegradable polyester elastomers in tissue engineering," Expert Opin. Biol. Ther. 4(6):801-812 (2004).
Zhong, S.P., et al., "Development of a novel collagen-GAG nanofibrous scaffold via electrospinning," Materials Science and Engineering: C, 27(2):262-266 (Mar. 2007) (available online Jun. 8, 2006).
Li, C., et al., "Electrospun silk-BMP-2 scaffolds for bone tissue engineering," Biomaterials, 27(16):3115-3124 (Jun. 2006) (available online Feb. 3, 2006).

(56) References Cited

OTHER PUBLICATIONS

Martins, A., et al., "Biodegradable nanofibers-reinforced microfibrous composite scaffolds for bone tissue engineering," Tissue Engineering: Part A, 16(12):3599-3609 (2010) (published online Sep. 21, 2010).

Yi, F., et al., "Poly(glycerol sebacate) nanofiber scaffolds by core/shell electrospinning," Macromol. Biosci. 8:803-806 (2008).

Sondell M, Lundborg G, Kanje M. Regeneration of the rat sciatic nerve into allografts made acellular through chemical extraction. Brain Res Jun. 8, 1998;795(1-2):44-54.

Guan YQ, Tao HM, Li YC, Wang WW, Li ZB, Peng CL. Preparation and activity of a nanometer anti-microbial polyurethane. Journal of Wuhan University of Technology—Materials Science Edition 2009;24(4):540-545.

Wang, Y., et al., "In vivo degradation characteristics of poly(glycerol sebacate)," J. Biomed Mater Res A, 66(1):192-197 (Jul. 1 2003) (published online Jun. 10, 2003).

Sant, S., et al., "Fabrication and characterization of tough elastomeric fibrous scaffold applications," Conf. Proc. IEEE Eng. Med. Biol. Soc. 2010:3546-3548, and 32nd Annual International Conference of the IEEE EMBS Buenos Aires, Argentina, (Aug. 31-Sep. 4, 2010).

Ifkovits, J.L., et al., "Biodegradable and radically polymerized elastomers with enhanced processing capabilities," Biomed Mater. 3(3):034104 (Sep. 2008) (published Aug. 8, 2008).

Ifkovits, J.L., et al., "Biodegradable fibrous scaffolds with tunable properties formed from photo-cross-linkable poly(glycerol sebacate)," ACS Appl. Mater. Interfaces 1(9):1878-1886 (Sep. 2009; published online Sep. 11, 2009).

Schofer, M.D., et al., "Characterization of a PLLA-collagen I blend nanofiber scaffold with respect to growth and osteogenic differentiation of human mesenchymal stem cells," ScientificWorldJournal 9:118-129 (Feb. 15, 2009).

Venugopal, J.R., et al., "Nanobioengineered electrospun composite nanofibers and osteoblasts for bone regeneration," Artif. Organs 32(5):388-397 (2008).

Yang, X., et al., "Acceleration of osteogenic differentiation of preosteoblastic cells by chitosan containing nanofibrous scaffolds," Biomacromolecules 10(10):2772-2778 (Sep. 10, 2009).

Heydarkhan-Hagvall, S., et al., "Three-dimensional electrospun ECM-based hybrid scaffolds for cardiovascular tissue engineering," Biomaterials 29(19):2907-2914 (Jul. 2008; available online Apr. 9, 2008).

Wang S, Wan AC, Xu X, Gao S, Mao HQ, Leong KW, et al. A new nerve guide conduit material composed of a biodegradable poly(phosphoester). Biomaterials May 2001;22(10):1157-1169.

Jeong, C.G., et al., "Mechanical, permeability, and degradation properties of 3D designed poly(1,8 octanediol-co-citrate) scaffolds for soft tissue engineering," J. Biomed. Mater. Res. Part B: Appl. Biomater. 93(1):141-149 (Apr. 2010; published online Jan. 20, 2010).

Wang, J., et al., "Spiral-structured, nanofibrous, 3D scaffolds for bone tissue engineering," J. Biomed. Mater. Res. A 93:753-762 (2010; published online Jul. 29, 2009).

Qiu, H., et al., "A citric acid-based hydroxyapatite composite for orthopedic implants," Biomaterials 27:5845-5854 (2006) (available online Aug. 21, 2006).

Nair, L.S., et al., "Nanofibers and nanoparticles for orthopaedic surgery applications," J. Bone Joint Surg. Am. 90(Supp. 1):128-131 (2008).

Abdel-Fattah, W.I., et al., "Synthesis, characterization of chitosans and fabrication of sintered chitosan microsphere matrices for bone tissue engineering," Acta Biomaterialia 3:503-514 (2007).

Li, M., et al., "Electrospun blends of natural and synthetic polymers as scaffolds for tissue engineering," Conf. Proc. IEEE Eng. Med. Biol. Soc. 6:5858-5861 (2005), 1 sheet abstract.

Yang, X., et al., "Multifunctional nanofibrous scaffold for tissue engineering," Journal of Experimental Nanoscience 3(4):329-345 (2008).

Deng, M., et al., "Biomimetic, bioactive etheric polyphosphazene-poly(lactide-co-glycolide) blends for bone tissue engineering," J. Biomed Mater Res A 92:114-125 (2010; published online Jan. 22, 2009).

Krogman, N.R., et al., "Hydrogen bonding in blends of polyesters with dipeptide-containing polyphosphazenes," J. Appl. Polym. Sci. 115:431-437 (2010; published online Sep. 1, 2009).

Wang W, Itoh S, Matsuda A, Ichinose S, Shinomiya K, Hata Y, et al. Influences of mechanical properties and permeability on chitosan nano/microfiber mesh tubes as a scaffold for nerve regeneration. J Biomed Mater Res A Feb. 2008;84(2):557-566.

Yang, J., et al., "Synthesis and evaluation of poly(diol citrate) biodegradable elastomers," Biomaterials 27:1889-1898 (2006; available online Nov. 15, 2005).

Yoshimoto, H., et al., "A biodegradable nanofiber scaffold by electrospinning and its potential for bone tissue engineering," Biomaterials 24(12):2077-2082 (May 2003).

Ndreu, A., et al., "Electrospun biodegradable nanofibrous mats for tissue engineering," Nanomedicine (Lond.) 3(1):45-60 (Feb. 2008), 1 sheet abstract.

Kim, S.S., et al., "Accelerated bonelike apatite growth on porous polymer/ceramic composite scaffolds in vitro," Tissue Eng. 12(10):2997-3006 (Oct. 2006).

Li, M., et al., "Electrospun protein fibers as matrices for tissue engineering," Biomaterials 26(30):5999-6008 (Oct. 2005) (available online May 13, 2005).

Kidoaki, S., et al., "Mesoscopic spatial designs of nano- and microfiber meshes for tissue-engineering matrix and scaffold based on newly devised multilayering and mixing electrospinning techniques," Biomaterials 26(1):37-46 (Jan. 2005) (available online Mar. 2, 2004).

Ma, Z., et al., "Potential of nanofiber matrix as tissue-engineering scaffolds," Tissue Engineering 11(1/2):101-109 (2005).

Li, W.J., et al., "Fabrication and characterization of six electrospun poly(alpha-hydroxy ester)-based fibrous scaffolds for tissue engineering applications," Acta Biomater. 2(4):377-385 (Jul. 2006; published online May 6, 2006).

Smith, L.A., et al., "Nano-fibrous scaffolds for tissue engineering," Colloids and Surfaces B: Biointerfaces 39(3):125-131 (Dec. 10, 2004; available online Feb. 4, 2004).

Smith, I.O., et al., "Nanostructured polymer scaffolds for tissue engineering and regenerative medicine," Interdisciplinary Reviews: WIREs Nanomed. Nanobiotechnol. 1(2):226-236 (Mar./Apr. 2009) (Jan. 12, 2009).

Wang, W., et al., "Biodegradable polyurethane based on random copolymer of L-lactide and $\varepsilon$-caprolactone and its shape-memory property," J. Appl. Polym. Sci. 104:4182-4187 (2007).

Guan, J., et al., "Preparation and characterization of highly porous, biodegradable polyurethane scaffolds for soft tissue applications," Biomaterials 26:3961-3971 (2005; available online Dec. 8, 2004).

Soletti, L., et al., "A bilayered elastomeric scaffold for tissue engineering of small diameter vascular grafts," Acta Biomaterialia 6:110-122 (2010; available online Jun. 18, 2009).

Ranganathan, S.I., et al., "Shaping the micromechanical behavior of multi-phase composites for bone tissue engineering," Acta Biomaterial 6:3448-3456 (2010; available online Mar. 24, 2010).

Lahiri, D., et al., "Boron nitride nanotube reinforced polylactide-polycaprolactone copolymer composite: Mechanical properties and cytocompatibility with osteoblasts and macrophages in vitro," Acta Biomaterialia 6:3524-3533 (2010; available online Mar. 10, 2010).

Misra, S.K., et al., "Characterization of carbon nanotube (MWCNT) containing P(3HB)/bioactive glass composites for tissue engineering applications," Acta Biomaterialia 6:735-742 (2010; available online Oct. 1, 2009).

Kim, H.W., et al., "Bioactive glass nanofiber-collagen nanocomposite as a novel bone regeneration matrix," J. Biomed. Mater. Res. A 79:698-705 (2006; published online Jul. 18, 2006).

Nair, L.S., et al., "Biodegradable polymers as biomaterials," Prog. Polym. Sci. 32:762-798 (2007; available online Jun. 11, 2007).

Zhang, Y., et al., "Electrospun biomimetic nanocomposite nanofibers of hydroxyapatite/chitosan for bone tissue engineering," Biomaterials 29:4314-4322 (2008; available online Aug. 20, 2008).

(56) References Cited

OTHER PUBLICATIONS

Venugopal, J., et al., "Biomimetic hydroxyapatite-containing composite nanofibrous substrates for bone tissue engineering," Phil. Trans. R. Soc. A 368:2065-2081 (2010).
Wan, Y., et al., "Biphasic scaffold for annulus fibrosus tissue regeneration," Biomaterials 29:643-652 (2008; available online Nov. 13, 2007).
Wang, C., et al., "Correlation between processing parameters and microstructure of electrospun poly(D,L-lactic acid) nanofibers," Polymer 50:6100-6110 (Nov. 2009; available online Oct. 30, 2009).
Um, I.C., et al., "Electro-spinning and electro-blowing of hyaluronic acid," Biomacromolecules 5:1428-1436 (2004; published online May 7, 2004).
Liu, Y., et al., "Electrospinning of poly(ethylene-co-vinyl acetate)/clay nanocomposite fibers," J. Polym. Sci.: Part B: Polym. Phys. 47:2501-2508 (Dec. 2009; first published online Nov. 10, 2009).
Ji, Y., et al., "Electrospun three-dimensional hyaluronic acid nanofibrous scaffolds," Biomaterials 27:3782-3792 (2006; available online Mar. 23, 2006).
Liu, Y., et al., "Engineering of bio-hybrid materials by electrospinning polymer-microbe fibers," P. Natl. Acad. Sci. USA 106(34):14201-14206 (Aug. 25, 2009).
Krogman, N.R., et al., "The influence of side group modification in polyphosphazenes on hydrolysis and cell adhesion of blends with PLGA," Biomaterials 30:3035-3041 (2009; available online Apr. 5, 2009).
Sethuraman, S., et al., "Novel low temperature setting nanocrystalline calcium phosphate cements for bone repair: Osteoblast cellular response and gene expression studies," J. Biomed. Mater. Res. A 82:884-891 (2007; published online Mar. 2, 2007).
Ren, L., et al., "Fabrication of gelatin-siloxane fibrous mats via sol-gel and electrospinning procedure and its application for bone tissue engineering," Materials Science and Engineering C 30:437-444 (2010; available online Jan. 11, 2010).
Douglas, T., et al., "Novel ceramic bone replacement material CeraBall∟ seeded with human mesenchymal stem cells," Clin. Oral Impl. Res. 21:262-267 (2010).
Shah, P.N., et al., "Electrospinning of L-tyrosine polyurethanes for potential biomedical applications," Polymer 50:2281-2289 (May 2009; available online Mar. 19, 2009).
Hong, Y, et al., "Preparation, bioactivity, and drug release of hierarchical nanoporous bioactive glass ultrathin fibers," Adv. Mater. 22:754-758 (2010).
Lu, X.L., et al., "Shape memory property of poly(L-lactide-co-?-caprolactone) copolymers," Materials Science and Engineering A 438-440:857-861 (2006).
Leonelli, C., et al., "Synthesis and characterization of cerium-doped glasses and in vitro evaluation of bioactivity," Journal of Non-Crystalline Solids 316:198-216 (2003).
Hersh, R.E., et al., "A technique for the treatment of sternal infections using the vacuum assisted closure™ device", Heart Surg. Forum, 4(3):211-15 (2001).
Sjogren, J., et al., "Vacuum-assisted closure therapy in mediastinitis after heart transplantation", J. Heart Lung Transplant., 23(4):506-7 (Apr. 2004).
Ostergaard L, Kristiansen SB, Angleys H, et al. The role of capillary transit time heterogeneity in myocardial oxygenation and ischemic heart disease. Basic Res Cardiol May 2014;109(3):409.
Thompson BC, Richardson RT, Moulton SE, Evans AJ, O'Leary S, Clark GM, et al. Conducting polymers, dual neurotrophins and pulsed electrical stimulation—Dramatic effects on neurite outgrowth. J Control Release Sep. 27, 2009.
Yang et al., "Electrospinning of nano/micro scale poly(L-lactic acid) aligned fibers and their potential in neural tissue engineering," Biomaterials 260:2603-2610 (2005).
International Search Report from International Application No. PCT/US2013/066747, dated Dec. 20, 2013.
Written Opinion from International Application No. PCT/US2013/066747, dated Dec. 20, 2013.

Supplementary European Search Report for EP13849526 dated May 25, 2016.
International Search Report and Written Opinion from International Application No. PCT/US15/54484 dated Jan. 6, 2016.
Wang, R et al. "Evaluation of Repeated Biphasic Conducting Materials for Peripheral Nerve Repair" and "Injectable and Self-Assembling Sponge As A Protective Layer At Device-Tissue Interfaces in Wound Repair." BMES, 12th Annual Graduate Student Research Symposium. May 16, 2013.
Merle M, Dellon AL, Campbell JN, Chang PS. Complications from silicon-polymer intubulation of nerves. Mircrosurgery 1989; 10(2):130-133.
Murphy CJ, Jana NR. Controlling the aspect ratio of inorganic nanorods and nanowires. Adv Mater Jan. 2002;14(1):80-82.
Li J, Ma PC, Chow WS, To CK, Tang BZ, Kim JK. Correlations between percolation threshold, dispersion state, and aspect ratio of carbon nanotubes. Advanced Functional Materials 2007;17(16):3207-3215.
Hernandez JJ, Garcia-Gutierrez MC, Nogales A, Rueda DR, Kwiatkowska M, Szymczyk A, et al. Influence of preparation procedure on the conductivity and transparency of SWCNT-polymer nanocomposites. Composites Science and Technology 2009;69(11-12):1867-1872.
Kostarelos K. The long and short of carbon nanotube toxicity. Nature Biotechnology 2008;26(7):774-776.
Lam CW, James JT, McCluskey R, Arepalli S, Hunter RL. A review of carbon nanotube toxicity and assessment of potential occupational and environmental health risks. Critical Reviews in Toxicology 2006;36(3):189-217.
Zhang XP, Sun BQ, Friend RH, Guo HC, Nau D, Giessen H. Metallic photonic crystals based on solution-processible gold nanoparticles. Nano Lett Apr. 2006;6(4):651-655.
Meek MF, Coert JH. Clinical use of nerve conduits in peripheral-nerve repair: review of the literature. J Reconstr Microsurg Feb. 2002;18(2):97-109.
Kalbacova M, Kalbac M, Dunsch L, Kataura H, Hempel U. The study of the interaction of human mesenchymal stem cells and monocytes/macrophages with single-walled carbon nanotube films. Phys Status Solidi B-Basic Solid State Phys Nov. 2006;243(13):3514-3518.
Kalbacova M, Kalbac M, Dunsch L, Kromka A, Vanecek M, Rezek B, et al. The effect of SWCNT and nano-diamond films on human osteoblast cells. Phys Status Solidi B-Basic Solid State Phys 2007;244(11):4356-4359.
Mitsumoto H, Tsuzaka K. Neurotrophic factors and neuromuscular disease: I. General comments, the neurotrophin family, and neuropoietic cytokines. Muscle Nerve Aug. 1999;22(8):983-999.
Jones DM, Tucker BA, Rahimtula M, Mearow KM. The synergistic effects of NGF and IGF-1 on neurite growth in adult sensory neurons: convergence on the PI 3-kinase signaling pathway. J Neurochem Sep. 2003;86(5):1116-1128.
Sakiyama-Elbert SE, Hubbell JA. Controlled release of nerve growth factor from a heparin-containing fibrin-based cell ingrowth matrix. J Control Release Oct. 3, 2000;69(1):149-158.
Webber CA, Xu Y, Vanneste KJ, Martinez JA, Verge VM, Zochodne DW. Guiding adult Mammalian sensory axons during regeneration. J Neuropathol Exp Neurol Mar. 2008;67(3):212-222.
Xu X, Yee WC, Hwang PY, Yu H, Wan AC, Gao, et al. Peripheral nerve regeneration with sustained release of poly(phosphoester) microencapsulated nerve growth factor within nerve guide conduits. Biomaterials Jun. 2003;24(13):2405-2412.
Ohta M, Suzuki Y, Chou H, Ishikawa N, Suzuki S, Tanihara M, et al. Novel heparin/alginate gel combines with basic fibroblast growth factor promotes nerve regeneration in rat sciatic nerve. J Biomed Mater Res A Dec. 15, 2004;71(4):661-668.
Winseck AK, Caldero J, Ciutat D, Prevette D, Scott SA, Wang G, et al. In vivo analysis of Schwann cell programmed cell death in the embryonic chick: regulation by axons and glial growth factor. J Neurosci Jun. 1, 2002;22(11):4509-4521.
Zurn AD, Winkel L, Menoud A, Djabali K, Aebischer P. Combined effects of GDNF, BDNF, and CNTF on motoneuron differentiation in vitro. J Neurosci Res Apr. 15, 1996;44(2):133-141.

(56) References Cited

OTHER PUBLICATIONS

Bailey SB, Eicheler ME, Villadiego A, Rich KM. The influence of fibronectin and laminin during Schwann cell migration and peripheral nerve regeneration through silicon chambers. J Neurocytol Mar. 1993;22(3):176-184.

Woolley AL, Hollowell JP, Rich KM. First place—Resident Basic Science Award 1990. Fibronectin-laminin combination enhances peripheral nerve regeneration across long haps. Otolaryngol Head Neck Surg Oct. 1990;103(4):509-518.

Li GN, Liu J, Hoffman-Kim D. Multi-molecular gradients of permissive and inhibitory cues direct neurite outgrowth. Ann Biomed Eng Jun. 2008;36(6):889-904.

Sta Iglesia DD, Cragoe EJ, Jr., Vanable JW, Jr. Electric field strength and epithelization in the newt (Notophthalmus viridescens). J Exp Zool Jan. 1, 1996;274(1):56-62.

Sta Iglesia DD, Vanalbe JW, Jr. Endogenous lateral electric fields around bovine corneal lesions are necessary for and can enhance normal rates of wound healing. Wound Repair Regen Nov-Dec. 1998;6(6):531-542.

Song B, Zhao M, Forrester J, McCaig C. Nerve regeneration and wound healing are stimulated and directed by an endogenous electrical field in vivo. Journal of Cell Science 2004;117(20):4681-4690.

Young PA, Young PH. Basic Clinical Neuroanatomy. Philedelphia: Lippincott Williams, and Wilkins, 1997.

Supronowicz PR, Ajayan PM, Ullmann KR, Arulanandam BP, Metzger DW, Bizios R. Novel current-conducting composite substrates for exposing osteoblasts to alternating current stimulation. J Biomed Mater Res Mar. 5, 2002;59(30):499-506.

Marsh G, Beams HW. In Vitro Contorl of Growing Chick Nerve Fibers by Applied Electric Currents. Journal of Cellular and Comparative Physiology 1946;27:139-157.

Macias MY, Battocletti JH, Sutton CH, Pintar FA, Maiman DJ. Directed and enhanced neurite growth with pulsed magnetic field stimulation. Bioelectromagnetics May 2000;21(4):272-286.

Zhao M, Dick A, Forrester JV, McCaig CD. Electric field-directed cell motility involves up-regulated expression and asymmetric redistribution of the epidermal growth factor receptors and is enhanced by fibronectin and laminin. Molecular Biology of the Cell 1999;10(4)1 259-1276.

Rajnicek AM, Robinson KR, McCaig CD. The direction of neurite growth in a weak DC electric field depends on the substratum: Contributions of adhesivity and net surface charge. Dev Biol Nov. 1998;203(2):412-423.

McCaig CD, Sangster L, Stewart R. Neurotrophins enhance electric field-directed growth cone guidance and directed nerve branching. Dev Dyn Mar. 2000;217(3):299-308.

MacKinnon SE, Dellon AL. Surgery of the Peripheral Nerve. Thieme Medical Publishers New York, 1988.

Wang S, Cai Q, Hou J, Bei J, Zhang T, Yang J, et al. Acceleration effect of basic fibroblast growth factor on the regeneration of peripheral nerve through a 15-mm gap. J Biomed Mater Res A Sep. 1, 2003;66(3):522-531.

Vleggeert-Lankamp CL. The role of evaluation methods in the assessment of peripheral nerve regeneration through synthetic conduits: a systematic review. Laboratory investigation. J Neurosurg Dec. 2007; 107(6):1168-1189.

Fine EG, Decosterd I, Papaloizos M, Zurn AD, Aebischer P. GDNF and NGF released by synthetic guidance channels support sciatic nerve regeneration across a long gap. Eur J Neurosci Feb. 2002;15(4):589-601.

Udina E, Furey M, Busch S, Silver J, Gordon T, Fouad K. Electrical stimulation of intact peripheral sensory axons in rats promotes outgrowth of their central projections. Exp Neurol Mar. 2008;210(1):238-247.

Al-Majed AA, Brushart TM, Gordon T. Electrical accelerates and increases expression of BDNF and trkB Mrna in regenerating rat femoral motoneurons. Eur J Neurosci Dec. 2000;12(12):4381-4390.

Zhang J, Lineaweaver WC, Oswald T, Chen Z, Zhang F. Ciliary neurotrophic factor for acceleration of peripheral nerve regeneration: an experimental study. J Reconstr Microsurg May 2004;20(4):323-327.

Varejao AS, Melo-Pinto P, Meek MF, Filipe VM, Bulas-Cruz J. Methods for the experimental functional assessment of rat sciatic nerve regeneration. Neurol Res Mar. 2004;26(2):186-194.

Varejao AS, Cabrita AM, Geuna S, Melo-Pinto P, Filipe VM, Gramsbergen A, et al. Toe out angle: a functional index for the evaluation of sciatic nerve recovery in the rat model. Exp Neurol Oct. 2003;183(20):695-699.

Subramanian et al, Development of biomaterial scaffold for nerve tissue engineering: Biomaterial mediated neural regeneration, Journal of Biomedical Science, 2009, 16, pp. 1-11.

Yu et al, Promoting neuron adhesion and growth, Materials today, 2008, 11, pp. 36-43.

Widmer et al, Manufacture of porous biodegradable polymer conduits by an extrusion process for guided tissue regeneration, Biomaterials, 1998, 19, pp. 1945-1955.

Chen et al, Development of biodegradable porous scaffolds for tissue engineering, Materials Science and Engineering C, 2001, 17, pp. 63-69.

Lee et al, In vivo conjunctiva! reconstruction using modified PLGA grafts for decreased scar formation and contraction, Biomaterials, 2003, 24, pp. 5049-5059.

Cytometrics, from http://www.nanomedicine.com/NMI/8.5.1.htm, pp. 1-2, accessed Jul. 5, 2016.

May, The Effects of Biological Wound Dressings on the Healing Process,National Tissue Services, American Red Cross, 1991;8(3-4):243-9.

Salisbury et al., Biological Dressings and Evaporative Water Loss from Burn Wounds, Annals of Plastic Surgery vol. S No. 4 Oct. 1980, pp. 270-272.

Calvin et al., Microstructure and Mechanics of the Chorioamnion Membrane with an Emphasis on Fracture Properties, vol. 1101, Reproductive Biomechanics pp. 166-185, Apr. 2007.

Tao Xua, et al., Viability and electrophysiology of neural cell structures generated by the inkjet printing method, Biomaterials 27 (2006) 3580-3588, Jan. 2006.

Scott J.Hollister, Porous scaffold design for tissue engineering, Nature Materials vol. 4 Jul. 2005.

Banani Kundu et al., Thromboelastometric and platelet responses to silk biomaterials, Scientific Reports, pp. 1-9, May 2014.

R. W. Farndale et al., The role of collagen in thrombosis and hemostasis, Journal of Thrombosis and Haemostasis, 2: 561-573.

Wei Wu, Ph.D. et al., Artificial Niche Combining Elastomeric Substrate and Platelets Guides Vascular Differentiation of Bone Marrow Mononuclear Cells, Tissue Engineering: Part A vol. 17, No. 15 and 16, 2011.

Journal of pressure ulcer, 2012, vol. 14, No. 1, p. 43-48.

\* cited by examiner

DEVICES AND METHODS FOR TREATING SPINAL CORD TISSUE

RELATED APPLICATIONS

This application is a continuation of U.S. application Ser. No. 14/458,790, filed Aug. 13, 2014, which is a divisional of U.S. application Ser. No. 12/248,346, filed Oct. 9, 2008, which issued as U.S. Pat. No. 8,834,520, which claims the benefit of priority of U.S. Provisional application Ser. No. 60/978,884, filed on Oct. 10, 2007, U.S. Provisional application Ser. No. 61/081,997, filed on Jul. 18, 2008, and U.S. Provisional application Ser. No. 61/088,558, filed on Aug. 13, 2008, the entire contents of which applications are incorporated herein by reference.

FIELD OF THE INVENTION

The present invention relates generally to devices and methods for treating damaged or compromised spinal cord tissue using sub-atmospheric pressure and more particularly, but not exclusively, to devices and methods for treating spinal cord tissue that have experienced a recoverable or non-recoverable injury.

BACKGROUND OF THE INVENTION

The anatomy, physiology, and pathologic processes that involve the spinal cord pose special concerns for the treatment of damaged or compromised spinal cord tissue. The preservation of both the three-dimensional structural anatomy and the microanatomical relationships of neurons (whose function depends on specific spatial relationships with other neurons and other supporting cells), as well as the maintenance of properly oxygenated blood flow and the homogeneous ground substance matrix in which the neurons survive, are vital to the survival and function of spinal cord tissues. Moreover, the inability of spinal cord cells to regenerate emphasizes the need to maximize survival of every possible neuron. For reasons such as these, treatment of both open and closed space pathology in the spinal cord poses special concerns.

Among the clinical problems that threaten survival of spinal cord tissue, the control of spinal cord edema, infection, and blood supply are central. The spinal cord responds to trauma and injury by collecting a significant amount of interstitial edema. Because the spinal cord is enclosed in a closed space (dura and the spinal canal), edema results in compression and compromise of the blood flow and nutritional performance of the spinal cord, which greatly impairs physiological recovery of the spinal cord and often of itself results in progression of compromise and death of the spinal cord. Currently available treatments for reducing edema include pharmacologic agents, such as glucocorticoids (Dexamethasone, Prednisone, Methyl Prednisolone), diuretics, and extensive surgical decompression. However, disadvantages to these treatments include irregular and unpredictable results, complications of the drugs, infection, and surgical complications.

The need for rapid and effective treatment is also vital due to the disastrous consequences and high likelihood of rapid propagation of infection and edema in the spinal cord. At present there are few successful methods available to treat pathologies affecting the intraspinal space, spinal cord parenchyma, and the surrounding structures. Where tissues elsewhere in the body can be treated with dressing changes, the spinal cord is not amenable to this type of treatment because of its precarious structure, propensity for infection, and potential for progression of injury. There is evidence that inflammation and immunological response to spinal cord trauma and other pathology are of equal or greater long term consequences than the initial trauma or insult. The response of the spinal cord to decreased blood flow secondary to edema results in hypoxia and ischemia/reperfusion-mediated injury. These injuries contribute to the neuropathological sequella, which greatly contribute to the adverse outcome of spinal injury.

In addition, the spinal cord requires a continuous supply of oxygenated blood to function and survive. Within a few minutes of complete interruption of blood flow to the spinal cord, irreversible spinal cord damage results. The spinal cord can, however, remain viable and recover from reduced blood flow for more prolonged periods. There is evidence that focal areas of the spinal cord can remain ischemic and relatively functionless for days and still recover. This finding has led to the concept of an ischemic zone, termed the penumbra or halo zone, that surrounds an area of irreversible injury. A secondary phenomena in the ischemic zone is the release of excitotoxins that are released locally by injured neurons, alterations in focal blood flow, and edema.

Vascular pathology of the spine may be a result of: inadequate blood flow to the spinal cord cells from decreased perfusion pressure, rupture of a blood vessel resulting in direct injury to the local spinal cord area, or by compression of adjacent tissue; intrinsic disease of the spinal cord blood vessels such as atherosclerosis, aneurysm, inflammation, etc.; or a remote thrombus that lodges in the spinal cord blood vessels from elsewhere such as the heart.

In cases of intraspinal hemorrhage, the hemorrhage usually begins as a small mass that grows in volume by pressure dissection and results in displacement and compression of adjacent spinal cord tissue. Edema in the adjacent compressed tissue around the hemorrhage may lead to a mass effect and a worsening of the clinical condition by compromising a larger area of spinal cord tissue. Edema in the adjacent spinal cord may cause progressive deterioration usually seen over 12 to 72 hours. The occurrence of edema in the week following the intraspinal hemorrhage often worsens the prognosis, particularly in the elderly. The tissue surrounding the hematoma is displaced and compressed but is not necessarily fatally compromised. Improvement can result as the hematoma is resorbed, adjacent edema decreased, and the involved tissue regains function.

Treatment of these conditions has been disappointing. Surgical decompression of the spinal cord can be helpful in some cases to prevent irreversible compression. Agents such as mannitol and some other osmotic agents can reduce intraspinal pressure caused by edema. Steroids are of uncertain value in these cases, and recently hyperbaric oxygen has been proposed.

Thus, though the application of negative (or sub-atmospheric) pressure therapy to wounded cutaneous and subcutaneous tissue demonstrates an increased rate of healing compared to traditional methods (as set forth in U.S. Pat. Nos. 5,645,081, 5,636,643, 7,198,046, and 7,216,651, as well as US Published Application Nos. 2003/0225347, 2004/0039391, and 2004/0122434, the contents of which are incorporated herein by reference), there remains a need for devices and methods specifically suited for use with the specialized tissues of the spinal cord.

SUMMARY OF THE INVENTION

The present invention provides devices and methods that use sub-atmospheric (or negative) pressure to treat damaged spinal cord tissue, such as spinal tissue damaged by disease, infection, or trauma, for example, which may lead to the presence of swelling, compression, and compromised blood flow secondary to interstitial edema. For instance, the spinal cord may be damaged by blunt trauma resulting in a recoverable or non-recoverable injury.

In one of its aspects the present invention provides a method for treating damaged spinal cord tissue using sub-atmospheric pressure. The method comprises locating a porous material proximate the damaged spinal cord tissue to provide gaseous communication between one or more pores of the porous material and the damaged spinal cord tissue. The porous material may be sealed in situ proximate the damaged spinal cord tissue to provide a region about the damaged spinal cord tissue for maintaining sub-atmospheric pressure at the damaged spinal cord tissue. The porous material may be operably connected with a vacuum system for producing sub-atmospheric pressure at the damaged spinal cord tissue, and the vacuum system activated to provide sub-atmospheric pressure at the damaged spinal cord tissue. The sub-atmospheric pressure may be maintained at the damaged spinal cord tissue for a time sufficient to decrease edema at the spinal cord. For example, the sub-atmospheric pressure may be maintained at about 25 mm Hg below atmospheric pressure. The method may also include locating a cover over damaged spinal cord tissue and sealing the cover to tissue proximate the damaged spinal cord tissue for maintaining sub-atmospheric pressure at the damaged spinal cord tissue. The cover may be provided in the form of a self-adhesive sheet which may be located over the damaged spinal cord tissue. In such a case, the step of sealing the cover may include adhesively sealing and adhering the self-adhesive sheet to tissue surrounding the damaged spinal cord tissue to form a seal between the sheet and tissue surrounding the damaged spinal cord tissue.

In another of its aspects the present invention provides an apparatus for treating damaged spinal cord tissue. The apparatus may include a porous bio-incorporable material, such as an open-cell collagen, having pore structure configured to permit gaseous communication between one or more pores of the porous material and the spinal cord tissue to be treated. The bio-incorporable nature of the porous material can obviate the need for a second procedure to remove the porous material. (As used herein the term "bio-incorporable" is defined to describe a material that may be left in the patient indefinitely and is capable of being remodeled, resorbed, dissolved, and/or otherwise assimilated or modified.) The apparatus also includes a vacuum source for producing sub-atmospheric pressure; the vacuum source may be disposed in gaseous communication with the porous material for distributing the sub-atmospheric pressure to the spinal cord tissue. The porous material may have, at least at a selected surface of the porous material, pores sufficiently small to prevent the growth of tissue therein. In addition, the porous material may have, at least at a selected surface of the porous material, a pore size smaller than the size of fibroblasts and spinal cord cells, and may have a pore size at a location other than the selected surface that is larger than that of fibroblasts and spinal cord cells. The pore size of the porous material may be large enough to allow movement of proteins the size of albumin therethrough. Also, the porous bio-incorporable material may include at least one surface that is sealed to prevent the transmission of sub-atmospheric pressure therethrough. The apparatus may also include a cover configured to cover the damaged spinal cord tissue to maintain sub-atmospheric pressure under the cover at the damaged spinal cord tissue.

Thus, the present invention provides devices and methods for minimizing the progression of pathologic processes, minimizing the disruption of physiological spinal cord integrity, and minimizing the interference with spinal cord blood flow and nutrition. By decreasing spinal cord edema and intraspinal pressure the risk of spinal cord herniation and compromise may be minimized. In addition, the present invention facilitates the removal of mediators, degradation products, and toxins that enhance the inflammatory and neuropathological response of tissues in the spinal cord.

BRIEF DESCRIPTION OF THE DRAWINGS

The foregoing summary and the following detailed description of the preferred embodiments of the present invention will be best understood when read in conjunction with the appended drawings, in which.

DETAILED DESCRIPTION OF THE INVENTION

Referring now to the figures, wherein like elements are numbered alike throughout, the present invention relates to devices and methods that use sub-atmospheric (or negative) pressure for treating damaged spinal cord tissue, where "damaged" tissue is defined to include tissue that is injured, compromised, or in any other way impaired, such as damage due to trauma, disease, infection, surgical complication, or other pathologic process, for example. More specifically, the devices and methods of the present invention can effect treatment of edema of the spinal cord parenchyma secondary to any cause, such as the aforementioned causes; treatment of any of the spaces surrounding the spinal cord, including the subdural/epidural spaces; and, treatment of elevated intraspinal pressure due to any cause, such as the aforementioned causes.

Figure 1:
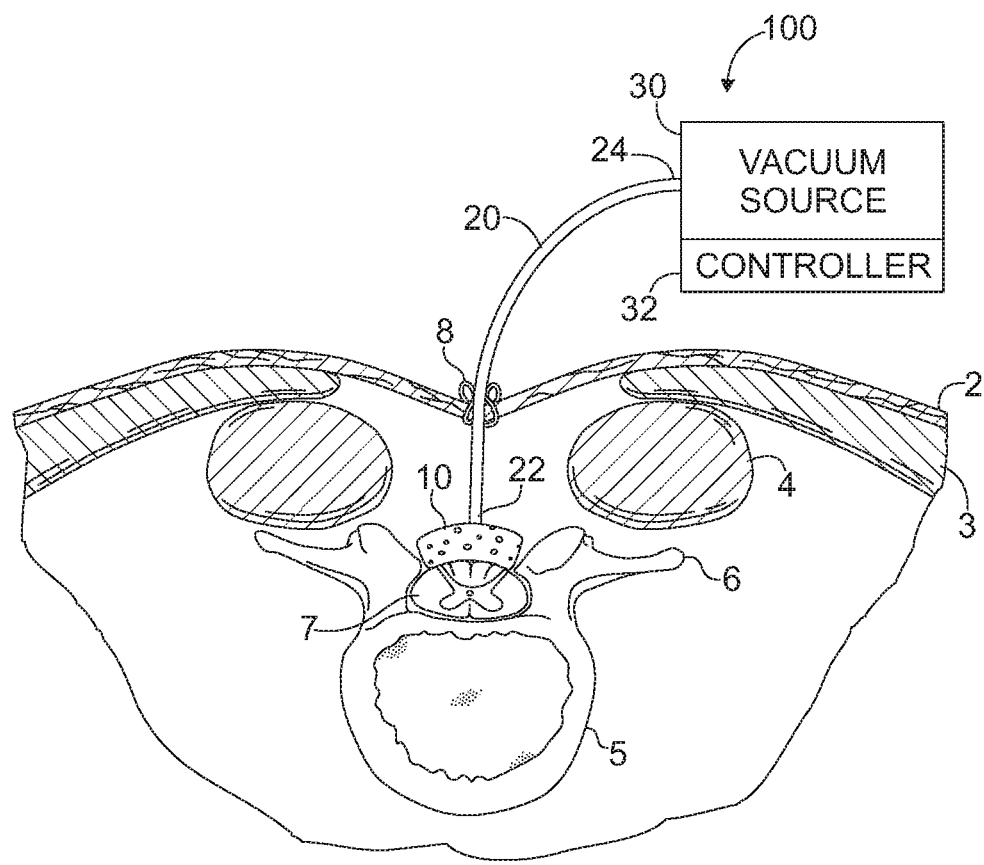
FIG. 1 schematically illustrates a partial cross-sectional view of an exemplary configuration of an apparatus of the present invention in situ prior to the application of sub-atmospheric pressure.
Figure 10:
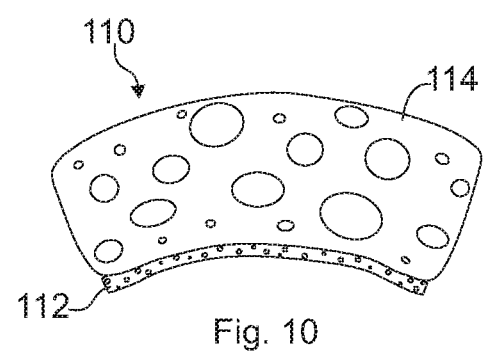
FIG. 10 schematically illustrates a porous material having a multi-layer structure for use in a sub-atmospheric pressure apparatus of the present invention.
Figure 2:
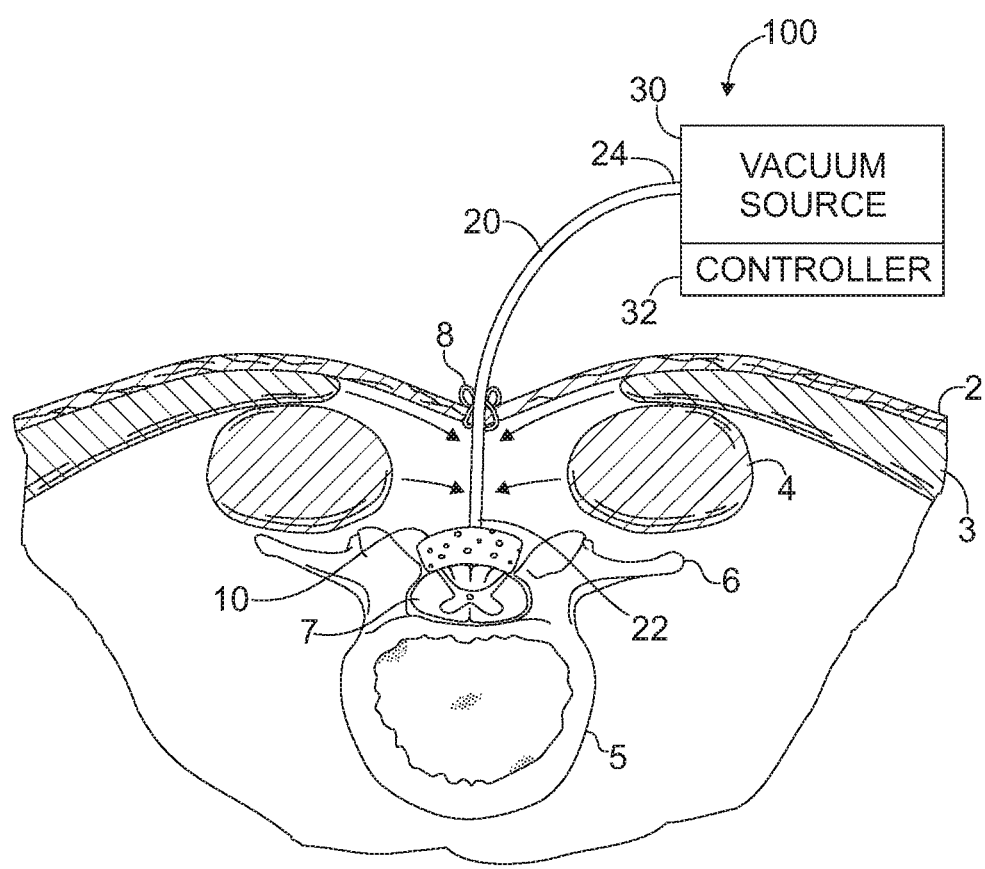
FIG. 2 schematically illustrates the partial cross-sectional view of FIG. 1 as a sub-atmospheric pressure is being applied.
Figure 3:
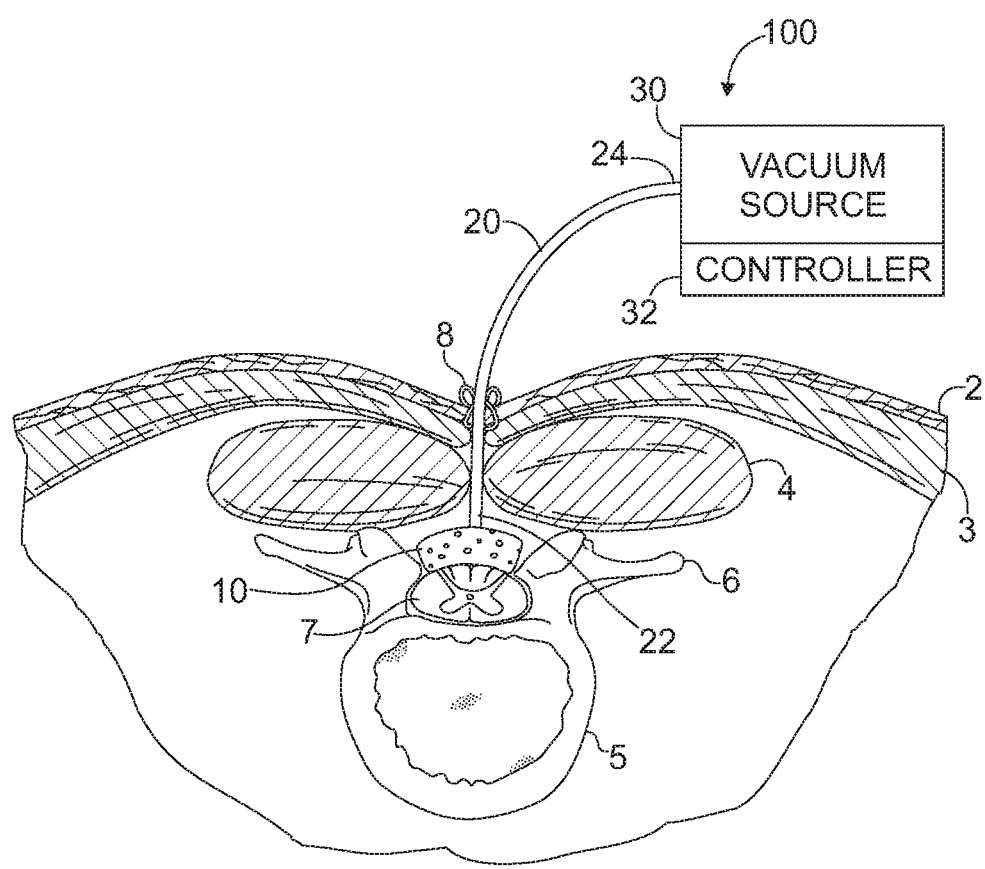
FIG. 3 schematically illustrates the partial cross-sectional view of FIGS. 1 and 2 showing the effect of the applied sub-atmospheric pressure on the tissues surrounding the spinal cord.

An exemplary configuration of a sub-atmospheric spinal cord treatment device 100 of the present invention may include a vacuum source 30 for supplying sub-atmospheric pressure via a tube 20 to a porous material 10 disposed proximate the spinal cord 7, FIGS. 1-3. In this regard, the porous material 10 may be structured to deliver and distribute sub-atmospheric pressure to the spinal cord 7. The spinal cord treatment device 100 may be applied to a patient by locating a porous material 10 proximate the damaged spinal cord tissue 7 to provide gaseous communication between one or more pores of the porous material 10 and the damaged spinal cord tissue 7. A tube 20 may be connected to the porous material 10 at a distal end 22 of the tube 20, and the porous material 10 may be sealed in situ by sutures 8 in the skin and subcutaneous tissues 2 to provide a region about the damaged spinal cord tissue 7 for maintaining sub-atmospheric pressure. The proximal end 24 of the tube 20 may be attached to a vacuum source 30 to operably connect the porous material 10 to the vacuum system 30 for producing sub-atmospheric pressure at the damaged spinal cord tissue 7 upon activation of the vacuum system 30.

Turning to FIG. 1 in greater detail, an exemplary configuration of a sub-atmospheric spinal cord treatment device 100 of the present invention is illustrated in situ in a patient with surrounding tissues shown in partial cross-section. The tissues illustrated include the skin and subcutaneous tissue 2, muscle tissue, such as the trapezius 3 and erector spinae 4, vertebrae 5, transverse process 6, and the spinal cord 7. To provide access to the spinal cord 7, a portion of the vertebrae 5 may be missing. For instance, the spinous process may be absent due to surgical dissection, disease, or injury. A porous material 10, such as an open-cell collagen material, may be placed in the subcutaneous space proximate the spinal cord tissue 7 to be treated with sub-atmospheric pressure to decrease edema in the parenchymal tissues and improve physiologic function, for example. In addition to an open-cell collagen material, the porous material 10 may also include a polyglycolic and/or polylactic acid material, a synthetic polymer, a flexible sheet-like mesh, an open-cell polymer foam, a foam section, a porous sheet, a polyvinyl alcohol foam, a polyethylene and/or polyester material, elastin, hyaluronic acid, alginates, polydiolcitrates, polyhyrdoxybutyrate, polyhyrdoxyfumarate, polytrimethylenecarbonate, polyglycerolsebecate, aliphatic/aromatic polyanhydride, or other suitable materials, and combinations of the foregoing any of which may be fabricated by electrospinning, casting, or printing, for example. Such materials include a solution of chitosan (1.33% weight/volume in 2% acetic acid, 20 ml total volume) which may be poured into an appropriately sized mold. The solution is then frozen for 2 hours at −70° C., and then transferred to the lyophylizer with a vacuum applied for 24 hours. The material may be cross-linked by 2.5%-5% glutaraldehyde vapor for 12-24 hours (or by ultraviolet radiation for 8 hours) to provide a cast porous material 10.

Additionally, the porous material 10 may be made by casting polycaprolactone (PCL). Polycaprolactone may be mixed with sodium chloride (1 part caprolactone to 10 parts sodium chloride) and placed in a sufficient volume of chloroform to dissolve the components. For example, 8 ml of the solution may be poured into an appropriately sized and shaped contained and allowed to dry for twelve hours. The sodium chloride may then be leached out in water for 24 hours.

It is also possible to use electrospun materials for the porous material 10. One exemplary of a formulation and method for making an electrospun porous material 10 was made using a combination of collagen Type I:chondroitin-6-sulfate (CS): poly 1,8-octanediol citrate (POC) in a ratio of 76%:4%:20%: by weight. Two solvents were utilized for the collagen/CS/POC. The CS was dissolved in water and the collagen and POC were dissolved in 2,2,2-trifluoroethanol (TFE). A 20% water/80% TFE solution (volume/volume) solution was then used. For electrospinning, the solution containing the collagen:CS:POC mixture was placed in a 3 ml syringe fitted to an 18 Ga needle. A syringe pump (New Era Pump Systems, Wantaugh, N.Y.) was used to feed the solution into the needle tip at a rate of 2.0 ml/hr. A voltage of 10-20 kV was provided by a high voltage power supply (HV Power Supply, Gamma High Voltage Research, Ormond Beach Fla.) and was applied between the needle (anode) and the grounded collector (cathode) with a distance of 15-25 cm. The material was then cross-linked with glutaraldehyde (Grade II, 25% solution) and heat polymerized (80° C.) for 48 hours. It is also possible to electrospin collagen Type I porous materials 10 starting with an initial concentration of 80 mg/ml of collagen in 1,1,1,3,3,3-hexafluoro-2-propanol (HFP), then use the same electrospinning conditions as the collagen:CS:POC combination.

An additional method for creating porous materials 10 is to use thermal inkjet printing technologies. Bio-incorporable materials such as collagen, elastic, hyaluronic acid, alginates, and polylactic/polyglycolic acid co-polymers may be printed. As examples, Type I collagen (Elastin Products Co., Owensville, Mo.) dissolved in 0.05% acetic acid, then diluted to 1 mg/ml in water can be printed, as can sodium alginate (Dharma. Trading Co., San Raphael, Calif.) 1 mg/ml in water. A mixture of Type I collagen (2.86 mg/ml in 0.05% acetic acid) and polylactic/polyglycolic acid (PURAC America, Blair, Nebr.) (14.29 mg/ml in tetraglycol (Sigma Aldrich, St. Louis Mo.)) can also be printed. Hardware from a Hewlett Packard 660c printer, including the stepper motors and carriage for the cartridges, can be mounted to a platform. The height of the hardware above the platform can then be adjusted for printing in layers.

The porous material 10 may comprise pores sufficiently small at the interface between the porous material 10 and the spinal cord 7 to prevent the growth of tissue therein, e.g., a pore size smaller than the size of fibroblasts and spinal cord cells; otherwise the porous material 10 may stick to the spinal cord 7 and cause bleeding or trauma when the porous material 10 is removed. In addition, the pore size at the interface between the porous material 10 and the spinal cord 7 may be sufficiently small so as to avoid the excessive production of granulation or scar tissue at the spinal cord 7 which may interfere with the physiologic function of the spinal cord 7. At the same time, the pore size of the porous material 10 may be large enough to allow movement of proteins the size of albumin therethrough to permit undesirable compounds to be removed, such as mediators, degradation products, and toxins.

The porous material 10 may, however, have a larger pore size (e.g., larger than that of fibroblasts and spinal cord cells) interior to the porous material 10 or at any other location of the porous material 10 that is not in contact with spinal cord tissue 7. For example, the porous material 110 may comprise a multi-layer structure with a non-ingrowth layer 112 having a sufficiently small pore size to prevent the growth of tissue therein for placement at the spinal cord, and may have an additional layer 114 of a different material that has a relatively larger pore size in contact with the non-ingrowth layer 112.

Alternatively, the porous material 10 may be homogeneous in composition and/or morphology. At a location away from the interface with the spinal cord 7, the porous material 10 may have a pore size sufficiently large o promote the formation of granulation tissue at other tissues in the spaces surrounding the spinal cord 7, such as promotion of granulation tissue in areas where spinal cord disruption has occurred. In addition, the porous material 10 may have a configuration in which one or more sides or surfaces of the porous material 10 are sealed to prevent the transmission of sub-atmospheric pressure through such a sealed surface, while at the same time having at least one surface through which sub-atmospheric pressure may be transmitted. Such a configuration of the porous material 10 can present preferential treatment of tissue on one side of the porous material 10 while not treating the other side. For instance, the parenchyma of the spinal cord 7 could be treated with the non-sealed interface on one side of the porous material 10.

The porous material 10 may be comprised of a material that needs to be removed after sub-atmospheric therapy is given, which could require a second surgery. Alternatively, the porous material 10 may be comprised of a material that is bioabsorbable or degrades harmlessly over time to avoid a second surgery, such as collagen. In addition, the porous material 10 may comprise a non-metallic material so that an MRI can be performed while the porous material 10 is in situ. The porous material 10 may also comprise a material that is sufficiently compliant so that if it presses against the spinal cord 7 the porous material 10 does not interfere with spinal cord function. At the same time, the porous material 10 may comprise a material that is sufficiently firm so that the porous material 10 does not collapsed so much as to create a pull on, or distortion of, the "normal spinal cord" that might interfere with spinal cord function.

To deliver sub-atmospheric pressure to the porous material 10 for distribution to the spinal cord 7, a tube 20 may be connected directly or indirectly in gaseous communication with the porous material 10 at the distal end 22 of the tube 20. For example, the distal end 22 of the tube 20 may be embedded in the porous material 10 or may be placed over the porous material 10. The distal end 22 of the tube 20 may also include one or more fenestrations to assist in delivering the sub-atmospheric pressure to the porous material 10 and the spinal cord 7. The tube 20 may extend through an opening in the skin and subcutaneous tissue 2 Which may be secured about the tube 20 with a suture 8 to assist in providing a seal about the tube 20. The proximal end 24 of the tube 20 may be operably connected to a vacuum source 30, such as a vacuum pump, to provide sub-atmospheric pressure that is transmitted via the tube 20 to the porous material 10 and the spinal cord 7.

The vacuum source 30 may include a controller 32 to regulate the production of sub-atmospheric pressure. For instance, the vacuum source 30 may be configured to produce sub-atmospheric pressure continuously or intermittently; e.g. the vacuum source 30 may cycle on and off to provide alternating periods of production and non-production of sub-atmospheric pressure. The duty cycle between production and non-production may be between 1 to 10 (on/off) and 10 to 1 (on/off). In addition, intermittent sub-atmospheric pressure may be applied by a periodic or cyclical waveform, such as a sine wave. The vacuum source 30 may be cycled after initial treatment to mimic a more physiologic state, such as several times per minute. The sub-atmospheric pressure may be cycled on-off as-needed as determined by monitoring of the pressure in the spinal cord 7. In general, the vacuum source 30 may be configured to deliver sub-atmospheric pressure between atmospheric pressure and 75 mm Hg below atmospheric pressure to minimize the chance that the sub-atmospheric pressure may result in bleeding into the spinal cord 7 or otherwise be deleterious to the spinal cord 7. The application of such a sub-atmospheric pressure can operate to remove edema from the spinal cord 7, thus preserving neurologic function to increase the probability of recovery and survival in a more physiologically preserved state.

Figure 4:
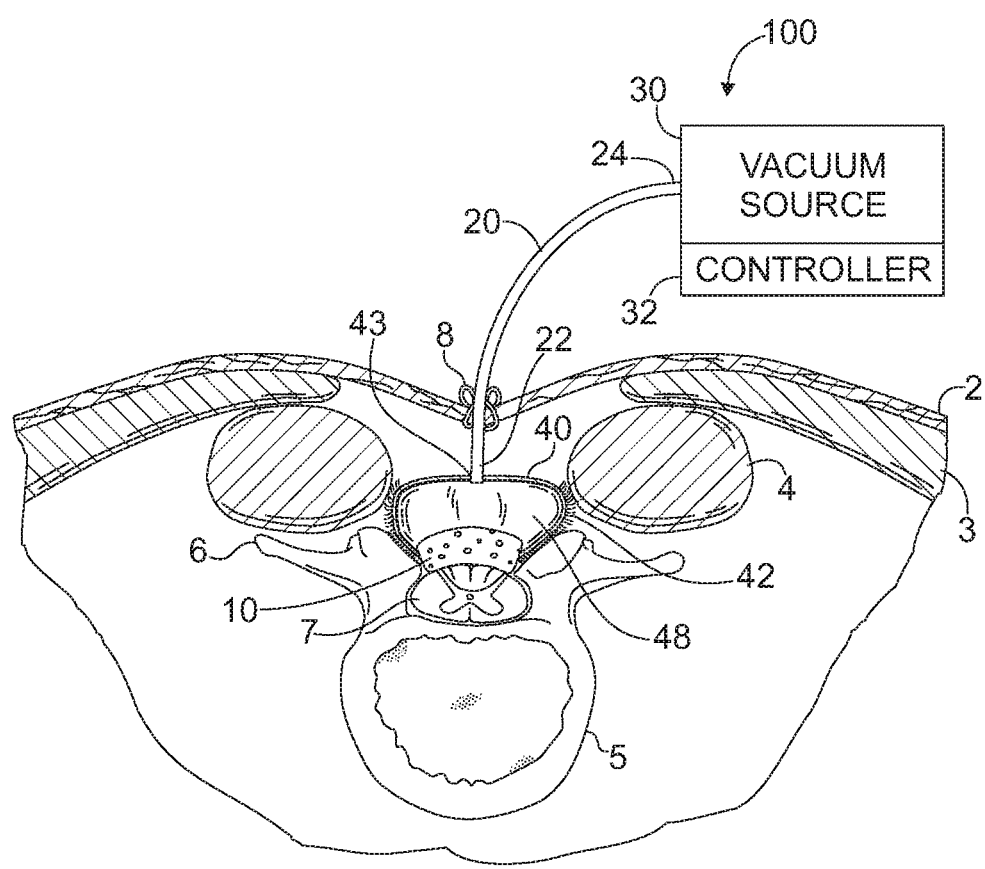
FIG. 4 schematically illustrates a partial cross-sectional view of a second exemplary configuration of the present invention in situ comprising a rigid or semi-rigid cover disposed subcutaneously over the spinal cord.
Figure 5:
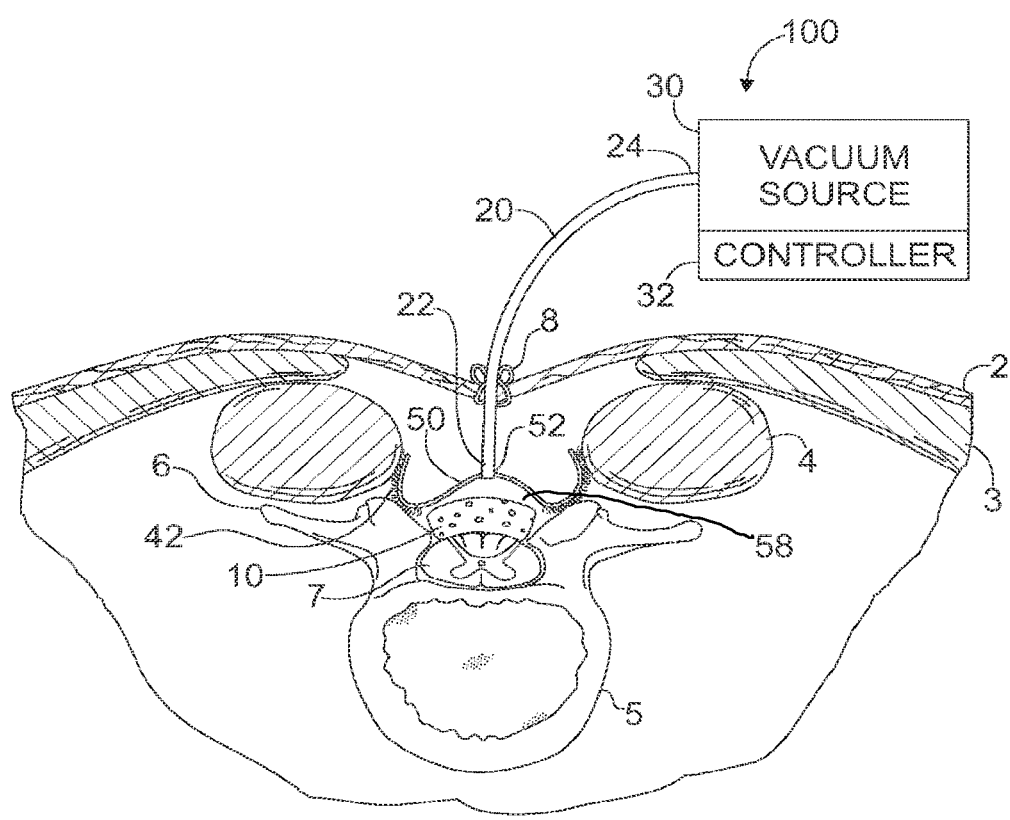
FIG. 5 schematically illustrates a partial cross-sectional view of a third exemplary configuration of the present invention in situ comprising a flexible cover disposed subcutaneously over the spinal cord.

To assist in maintaining the sub-atmospheric pressure at the spinal cord 7, a flexible cover/sheet 50 or rigid (or semi-rigid) cover 40 may be provided proximate the spinal cord 7 to provide a region about the spinal cord 7 where sub-atmospheric pressure may be maintained, FIGS. 4, 5. Specifically, with reference to FIGS. 4 and 5, a cover 40, 50 may be provided over the spinal cord 7 and porous material 10 by adhering the cover 40, 50 to tissues proximate the spinal cord 7 to define an enclosed region 48, 58 about the spinal cord 7 and porous material 10. For instance, the cover 40, 50 may be glued to the vertebrae 5, muscle tissue 4, and/or other appropriate tissues using an adhesive 42, such as a fibrin glue. The adhesive 42 may comprise an autopolymerizing glue and/or may desirably include a filler to provide the adhesive 42 with sufficient bulk to permit the adhesive 42 to conform to the shapes of the potentially irregular surfaces which the adhesive 42 contacts. The adhesive 42 may be provided as a separate component or as a portion of the cover 40, 50 to provide a self-adhesive cover 40, 50. For instance, the cover 50 may comprise a flexible self-adhesive sheet which includes a suitable adhesive on one or more of its surfaces.

For the flexible cover 50, an outside edge or border of the flexible cover 50 may be rolled under (or toward) the spinal cord 7. Alternatively, the flexible cover 50 may be curled out away from the spinal cord 7 so that the underside of the cover 50 (that side facing with the porous material 10) may then contact with the vertebrae 5 and surrounding muscles and soft tissue, FIG. 5. If the flexible cover 50 is rolled under the spinal cord 7, an adhesive 52 may then be applied to the outside of the cover 50 between the cover 50 and the vertebrae 5, surrounding muscle and soft tissues to help promote an airtight seal. If the flexible cover 50 is curled away from the spinal cord 7, an adhesive may be applied to the underside of the cover 50, between the cover 50 and the vertebrae 5 and surrounding muscle and soft tissue to create an airtight seal.

Sub-atmospheric pressure may be delivered under the cover 40, 50 by cooperation between the cover 40, 50 and the tube 20. Specifically, the cover 40 (or flexible cover 50) may include a vacuum port 43 to which the distal end 22 of the tube 20 connects to provide gaseous communication between the tube 20 and the space 48 under the cover 40 over the spinal cord 7, FIG. 4. Alternatively, the cover 50 (or cover 40) may include a pass-through 52 through which the tube 20 passes so that the distal end 22 of the tube 20 is disposed interior to, and in gaseous communication with, the space 58 under the cover 50 over the spinal cord 7. FIG. 5.

The cover 40, 50 may serve to further confine the subcutaneous region about the spinal cord 7 at Which sub-atmospheric pressure is maintained. That is, as illustrated in FIGS. 4 and 5, the cover 40, 50 provides an enclosed space/region 48, 58 about spinal cord 7 under the cover 40, 50, which can serve to isolate the tissues exterior to the cover 40, 50 from exposure to the sub-atmospheric pressure applied to the spinal cord 7. In contrast, as illustrated in FIGS. 2 and 3, in the absence of a cover, sub-atmospheric pressure delivered to the porous material 10 and spinal cord 7 may draw the surrounding tissues, such as muscles 3, 4, inward towards the tube 20 and porous material 10 along the directions of the arrows shown in FIG. 2 resulting in the configuration of tissues illustrated in FIG. 3. In this regard the stretched and/or moved tissues, such as muscles 3, 4, can help to confine the applied sub-atmospheric pressure to a region between the muscles 4 and the spinal cord 7. In addition the covers 40, 50 may further protect the spinal cord 7 from exogenous infection and contamination beyond the protection already afforded by the porous material 10 and sutured skin 2. Likewise, the covers 40, 50 may further protect surrounding tissues from the spread of infection from the spinal cord 7 such as spinal cord abscesses, meningitis, and spinal tissue infection.

In another of its aspects, the present invention also provides a method for treating damaged spinal cord tissue using sub-atmospheric pressure with, by way of example, the devices illustrated in FIGS. 1-5. In particular, the method may comprise locating a porous material 10 proximate the damaged spinal cord tissue 7 to provide gaseous communication between one or more pores of the porous material 10 and the damaged spinal cord tissue 7. The porous material 10 may be sealed in situ proximate the damaged spinal cord tissue 7 to provide a region about the damaged spinal cord tissue 7 for maintaining sub-atmospheric pressure at the damaged spinal cord tissue 7 In this regard, the muscles 3,4 and subcutaneous tissues may be loosely re-approximated over top of the porous material 10 with the tube 20 exiting through the skin 2 and the skin 2 sutured closed. A further airtight dressing may optionally be placed over the suture site to promote an airtight seal. The porous material 10 may be operably connected with a vacuum system 30 for producing sub-atmospheric pressure at the damaged spinal cord tissue 7, and the vacuum system 30 activated to provide sub-atmospheric pressure at the damaged spinal cord tissue 7. For example, the sub-atmospheric pressure may be maintained at about 25 to 75 mm Hg below atmospheric pressure. The sub-atmospheric pressure may be maintained at the damaged spinal cord tissue 7 for a time sufficient to decrease edema at the spinal cord 7 or to control spinal fluid leaks. In addition, the sub-atmospheric pressure may be maintained at the damaged spinal cord tissue 7 for a time sufficient to prepare the spinal cord tissue 7 to achieve a stage of healing and diminution of bacterial counts such that acceptance of secondary treatments (e.g., flaps, skin grafts) can be successful. The method may be used for at least 4 hours, or can be used for many days. At the end of the vacuum treatment, the sutures 8 may be removed and the skin 2 re-opened. The porous material 10 may then be removed and the skin 2 re-sutured closed.

The method may also include locating a cover 40, 50 over the damaged spinal cord tissue 7 and sealing the cover 40, 50 to tissue proximate the damaged spinal cord tissue 7 for maintaining sub-atmospheric pressure at the damaged spinal cord tissue 7. The step of sealing the cover 40, 50 to tissue surrounding the damaged spinal cord tissue 7 may comprise adhesively sealing and adhering the cover 40, 50 to tissue surrounding the damaged spinal cord tissue 7. The cover 50 may be provided in the form of a self-adhesive sheet 50 which may be located over the damaged spinal cord tissue 7. In such a case, the step of sealing the cover 50 may include adhesively sealing and adhering the self-adhesive sheet 50 to tissue surrounding the damaged spinal cord tissue 7 to form a seal between the sheet 50 and tissue surrounding the damaged spinal cord tissue 7. In addition, the step of operably connecting a vacuum system 30 in gaseous communication with the porous material 10 may comprise connecting the vacuum system 30 with the vacuum port 42 of the cover 40.

EXAMPLES

Rat Spinal Cord Injuries and Sub-atmospheric Pressure Exposure

Experiment 1

A series of experiments were conducted to determine the effects of sub-atmospheric pressure on the spinal cord in rats post contusion injury. In a first animal protocol, 250-300 gram Sprague Dawley rats were obtained and the model of spinal contusion developed and verified. The procedure for creating the injury and assessing recovery was based upon the description of spinal cord contusion injury in Wrathall, et al., Spinal Cord Contusion in the Rat: Production of Graded, Reproducible, Injury Groups, *Experimental Neurology* 88, 108-122 (1985). The surgical technique was developed for exposing the spinal cord in the anesthetized rats and consistent production of a contusion injury by dropping a cylindrical 10 gram weight through a glass tube from a height of 5 cm. Half of the rats were untreated controls while the other half had the area of contusion exposed to 4 hours of sub-atmospheric pressure (25 mm Hg below atmospheric). However, the degree of injury did not produce a significant injury in the control animals (they recovered quickly), and thus it was not possible to compare the treated animals to the control animals.

Experiment 2

A second protocol was developed in which a more severe injury was inflicted on the spinal cord (a 10 gram weight was dropped from a higher height—7.5 cm). Twenty-eight large (300 gram) Sprague Dawley rats were procured over rime and allowed to acclimate to housing conditions. On the day of surgery, the animals were sedated and the back shaved and scrubbed for surgery. A midline incision made over the spine was made extending through the skin and subcutaneous tissue and the cutaneous maximus muscle and fascia exposing the deeper back muscles. The paired muscles that meet at the midline (trapezius and potentially latisimus dorsi) were separated at the midline and retracted laterally. The deep 'postural' muscles such as the spinotrapezius and/or the sacrospinal muscles that are attached to the bony structures of the spine itself were also divided on the midline and retracted laterally. This exposed the spinous process and potentially some of the transverse processes. At the level of T7-T9, the spinous processes and the small transversospinal muscles that extend between two consecutive vertebra were removed, exposing the surface (dura) of the spinal cord. A laminectomy was performed at T-8. The spine was stabilized at T-7 and T-9 and a 10 gram weight was dropped from a height of 7.5 cm to produce a moderate degree of spinal cord injury based on the procedure of Wrathall, et al. Five animals died on their respective day of initial surgery (three in the control group and two in the vacuum treated group), and early in the experiment one animal in the control group died two days into the experiment, leaving 22 animals. By the end of the experiment, eleven animals had been assigned randomly to each of the control group and the 25 mm Hg vacuum group.

For the control rats, no treatment was provided, and the injury was sutured closed. For the vacuum treated rats, a polyvinyl alcohol vacuum dressing (Vacuseal Plus, Polymnedics, Belgium) was placed on the cord and the skin sutured closed, with the vacuum tube extending through the incision. After 1 hour delay, a vacuum (sub-atmospheric pressure) of 25 mm Hg below atmospheric pressure was applied for 4 hours to each animal in the vacuum treatment group. At the end of this time, the animals were re-sedated, the vacuum dressings removed, and the skin incision re-sutured with monofilament suture.

The incision sites were inspected daily. The animals were examined for signs of ability to self void their bladders. Any animal unable to void received manual assistance three times per day at 8 hour intervals. The animals were examined daily for signs of auto-cannibalism, pressure sores, and for degree of hydration (pinch test). The animals were housed in soft shavings to minimize potential for pressure sore development. Food was placed on the bottom of cages to facilitate eating. Animals were examined daily for recovery of motor function of hind limbs using a modified Tarlov scoring system for each hind limb. (0=no movement, no weight bearing; 1=slight movement, no weight bearing; 2=frequent movement, no weight bearing; 3=weight bearing, 1-2 steps; 4=walking with deficit; 5=walking with no deficit.) The animals were tested daily on an inclined plane (angle at which they can no longer hold on and slide off the plane), and for hind limb grip strength. The animals were euthanized 14 days post surgery, and the spines removed and examined histologically.

The results of the experiment are provided in Tables 1 and 2, with day "0" being the day of surgery. Several animals exhibited minimal injury/deficit and may not have had an adequate injury during weight drop. (Control animals 1, 2, 11 and treated animals 3, 9, 10. See Tables 1 and 2.) Two animals exhibited a severe/total injury and did not recover. (Control animal 5 and treated animal 2. See Tables 1 and 2.) This left a total of seven control and seven treated animals believed to have an adequate injury but not a severe/total injury.

For purposes of analysis, an animal was considered "recovered" as of the day on which it achieved a score of at least "4/4." Of the seven control animals, three had not recovered to at least a score of 4/4 (right leg/left leg—walking with deficit) by day eight post surgery. (Animals 3, 6, 7. Table 1.) Of the remaining four control animals (animals 4, 8, 9, 10), three animals reached a score of 4/4 on days 4, 6, and 13, and one reached a score of 4/5 on day 7. Thus, the four control animals reached a score of at least 4/4 in a mean of 7.5+/−3.35 days. For the treated animals, all seven (animals 1, 4, 5, 6, 7, 8, 11) reached a score of at least 4/4 in a mean of 5.14+/−1.24 days. Thus it is evident that application of 25 mm Hg vacuum to the injured spine was able to increase the rate of functional recovery (p=0.059).

TABLE 1

Control

| Animal | Time Post Surgery (days) | | | | | | | | |
|---|---|---|---|---|---|---|---|---|---|
| | 0 | 1 | 2 | 3 | 4 | 5 | 6 | 7 | 8 | 13 |
| 1 | 5/5 | 5/5 | 5/5 | 5/5 | 5/5 | 5/5 | 5/5 | 5/5 | 5/5 | |
| 2 | 5/4 | 5/4 | 5/4 | 5/4 | 5/4 | 5/4 | 5/4 | 5/4 | 5/4 | |
| 3 | 0/0 | 0/0 | 1/1 | 1/1 | 2/1 | 2/1 | 2/2 | 3/2 | 3/2 | |
| 4 | 2/2 | 2/2 | 3/3 | 3/3 | 4/4 | 4/4 | 4/4 | 5/4 | 5/4 | |
| 5 | 1/0 | 1/0 | 1/0 | 1/0 | 1/1 | 1/1 | 1/1 | 1/1 | 1/1 | |
| 6 | 0/0 | 0/0 | 1/0 | 1/0 | 1/1 | 2/1 | 2/2 | 3/2 | 3/2 | |
| 7 | 0/1 | 0/1 | 1/1 | 1/2 | 1/2 | 2/2 | 2/3 | 3/3 | 3/3 | |
| 8 | 0/0 | 0/0 | 1/1 | 1/1 | 2/2 | 2/2 | 3/3 | 3/3 | 3/3 | 4/4 |
| 9 | 0/0 | 0/0 | 0/1 | 0/1 | 1/2 | 2/2 | 3/4 | 4/5 | | |

TABLE 1-continued

Control

| Animal | Time Post Surgery (days) | | | | | | | | |
|---|---|---|---|---|---|---|---|---|---|
| | 0 | 1 | 2 | 3 | 4 | 5 | 6 | 7 | 8 | 13 |
| 10 | 0/0 | 0/0 | 1/1 | 1/1 | 1/1 | 1/1 | 4/4 | 4/4 | | |
| 11 | 4/4 | 4/4 | 5/4 | 5/5 | 5/5 | | | | | |

TABLE 2

Vacuum Treated

| Animal | Time Post Surgery (days) | | | | | | | | |
|---|---|---|---|---|---|---|---|---|---|
| | 0 | 1 | 2 | 3 | 4 | 5 | 6 | 7 | 8 | 13 |
| 1 | 1/1 | 1/2 | 1/2 | 2/2 | 3/4 | 4/4 | 4/4 | 4/4 | 4/4 | |
| 2 | 0/0 | 0/0 | 0/0 | 1/0 | 1/0 | 1/0 | 1/1 | 1/1 | 1/1 | |
| 3 | 4/4 | 4/5 | 5/5 | 5/5 | 5/5 | 5/5 | 5/5 | 5/5 | 5/5 | |
| 4 | 0.0 | 2/0 | 2/1 | 3/2 | 3/3 | 4/3 | 4/4 | 5/4 | 5/5 | |
| 5 | 2/1 | 2/1 | 3/2 | 3/3 | 4/4 | 5/5 | 5/5 | 5/5 | 5/5 | |
| 6 | 2/3 | 3/3 | 3/4 | 4/4 | 5/5 | 5/5 | 5/5 | 5/5 | 5/5 | |
| 7 | 1/0 | 1/0 | 1/1 | 2/3 | 3/4 | 4/5 | 5/5 | 5/5 | 5/5 | |
| 8 | 1/0 | 1/0 | 2/1 | 3/2 | 3/2 | 3/2 | 4/3 | 5/4 | 5/4 | 5/4 |
| 9 | 3/4 | 5/5 | 4/4 | 5/5 | 5/5 | | | | | |
| 10 | 4/4 | 4/4 | 4/4 | 5/5 | 5/5 | | | | | |
| 11 | 0/0 | 0/0 | 1/1 | 2/2 | 3/3 | 3/3 | 4/4 | 4/4 | | |

Experiment 3

An additional protocol was developed in which a still more severe injury was created that would result in a non-recoverable (permanent) functional deficit. The contusion paradigm was based upon techniques developed at the W. M. Keck Center for Collaborative Neuroscience—The Spinal Cord injury Project using the NYU spinal cord contusion system. These systems (currently named "MASCIS") are custom built and are available commercially through the Biology Department at Rutgers University (W. M. Keck Center for Collaborative Neuroscience, Piscataway, N.J.).

In the preceding experiments, animals were operated on depending on weight, but in this experiment the animals were operated on depending on age. Long Evans hooded rats were operated on at 77 days of age to standardize the severity of injury. Between one and six days before surgery, some of the animals were sedated and transpoited to the Small Animal MRI Imaging Facility of Wake Forest University School of Medicine, and the spinal cord was scanned at the level of T9-T10 using a Bruker Biospin Horizontal Bore 7 Tesla small animal scanner (Ettlingen, Germany). The animals which were scanned were then allowed to recover from anesthesia in a heated cage. On the day of surgery the animals were anesthetized, and the backs of the animals were shaved and a depilatory cream used. Using aseptic technique, a laminectomy was performed at the level of T9-T10. The NYU spinal cord contusion system impactor was used, and the cord was impacted at T9-T10 with a 10 gram rod dropped from a height of 25 mm. Animals in the control group had the incision sutured closed, and the animals were allowed to recover in a heated cage. For treated animals, a polyvinyl alcohol vacuum dressing (VersaFoam, Kinetic Concepts, Inc., San Antonio, Tex.) was placed over the cord, the incision sutured closed, and 25 mm Hg vacuum, i.e. 25 mm Hg below atmospheric pressure, applied for 8 hours. After this time the treated animals were re-sedated, the incision opened, the vacuum dressing removed, and the incision re-sutured closed. If the animals received a post-surgery MRI, the animal was scanned 8 hours post impaction.

Functional recovery was assessed with the BBB scale, a 22 point scale from the W. M. Keck Center for Collaborative Neuroscience. (Table 3). The animals were monitored for 21 days, then euthanized by lethal $CO_2$ exposure. Bladders were expressed daily, and the animals were monitored for signs of auto-cannibalism, pressure sores, skin lesions, etc. Any animal exhibiting signs of auto-cannibalization were removed from the study and euthanized. Pressure sores and skin lesions were treated as appropriate and with consultation of ARP veterinary staff. Despite this care, in the course of this experiment, some animals died, while others were excluded for other problems.

TABLE 3

BBB Locomotor Rating Scale

| Value | Condition |
|---|---|
| 0 | No observable hind limb (HL) movement |
| 1 | Slight Movement of one or two joints, usually the hip &/or knee |
| 2 | Extensive movement of one joint or Extensive movement of one joint and slight movement of one other joint |
| 3 | Extensive movement of two joints |
| 4 | Slight movement of all three joints of the HL |
| 5 | Slight movement of two joints and extensive movement of the third |
| 6 | Extensive movement of two joints and slight movement of the third |
| 7 | Extensive movement of all three joints of the HL |
| 8 | Sweeping with no weight support or Plantar placement of the paw with no weight support |
| 9 | Plantar placement of the paw with weight support in stance only (i.e. when stationary) or Occasional, Frequent, or Consistent weight supported dorsal stepping and no plantar stepping |
| 10 | Occasional weight supported plantar; no front limb (FL)-HL coordination |
| 11 | Frequent to consistent weight supported plantar steps and no FL-HL coordination |
| 12 | Frequent to consistent weight supported plantar steps and occasional FL-HL coordination |
| 13 | Frequent to consistent weight supported plantar steps and frequent FL-HL coordination |
| 14 | Consistent weight supported plantar steps, consistent FL-HL coordination and Predominant paw position during locomotion is rotated (internally or externally) when it makes initial contact with the surface as well as just before it is lifted off at the end of stance or Frequent plantar stepping; consistent FL-HL coordination; and occasional dorsal stepping |
| 15 | Consistent plantar stepping and Consistent FL-HL coordination; and No toe clearance or occasional toe clearance during forward limb advancement; Predominant paw position is parallel to the body at initial contact |
| 16 | Consistent plantar stepping and Consistent FL-HL coordination during gait; and Toe clearance occurs frequently during forward limb advancement; Predominant paw position is parallel at initial contact and rotated at lift off |
| 17 | Consistent plantar stepping and Consistent FL-HL coordination during gait; and Toe clearance occurs frequently during forward limb advancement; Predominant paw position is parallel at initial contact and lift off |
| 18 | Consistent plantar stepping and Consistent FL-HL coordination during gait; and Toe clearance occurs consistently during forward limb advancement; Predominant paw position is parallel at initial contact and rotated at lift off |
| 19 | Consistent plantar stepping and Consistent FL-HL coordination during gait; and Toe clearance occurs consistently during forward limb advancement; Predominant paw position is parallel at initial contact and lift off; and tail is down part or all of the time |
| 20 | Consistent plantar stepping and Consistent coordinated gait; consistent toe clearance' Predominant paw position is parallel at initial contact and lift off; and Trunk instability: Tail consistently up |
| 21 | Consistent plantar stepping and Consistent coordinated gait; consistent toe clearance; predominant paw position is parallel throughout stance; consistent trunk stability; tail consistently up |

Figure 6:
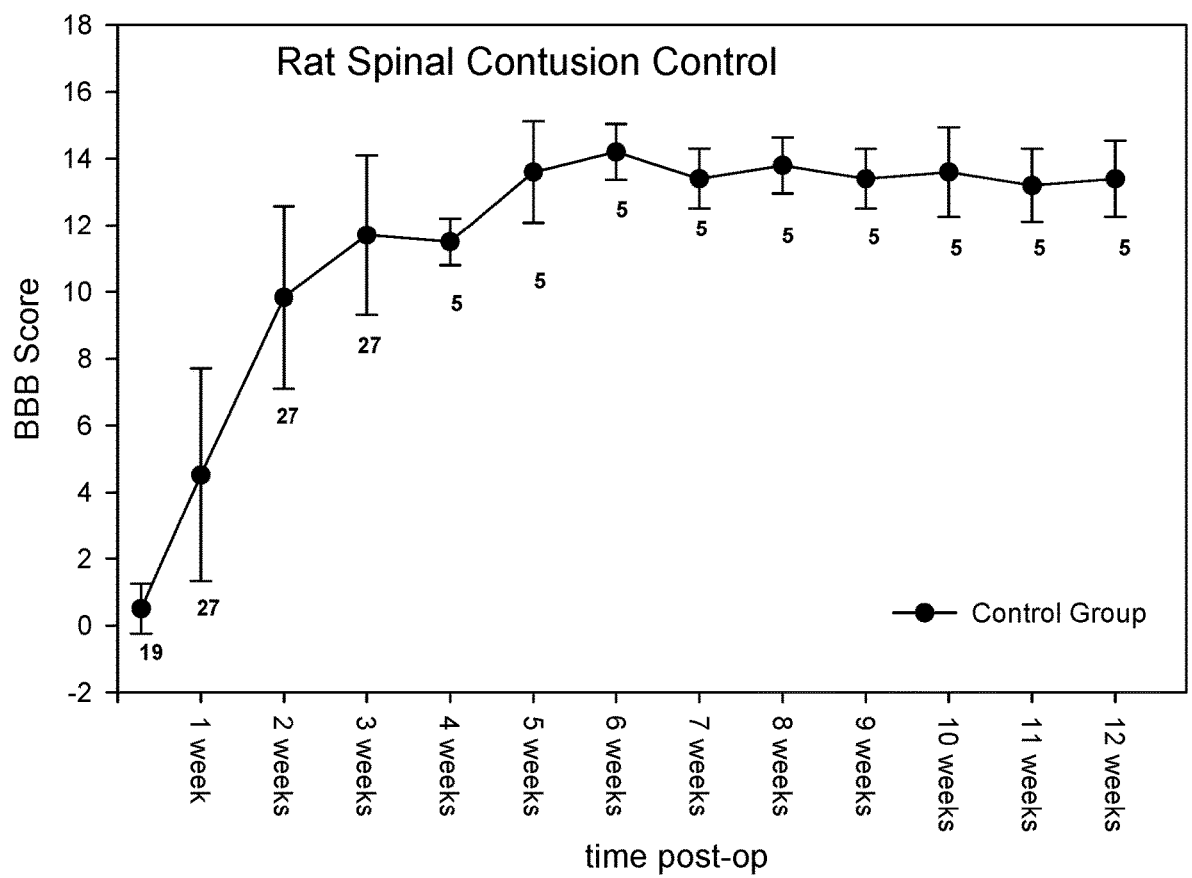
FIG. 6 illustrates the BBB score as a function of time for control animals exposed to recoverable blunt trauma of the spinal cord.
Figure 7:
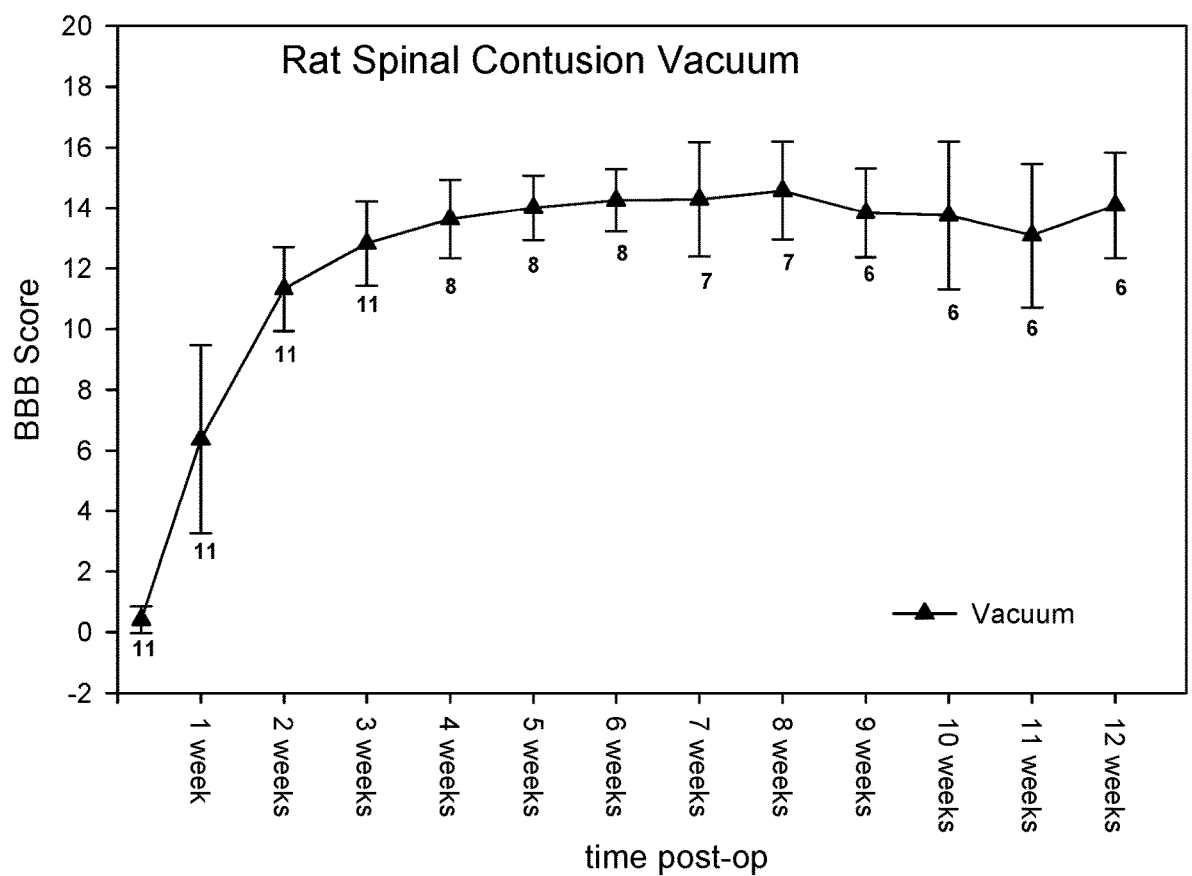
FIG. 7 illustrates the BBB score as a function of time for animals exposed to recoverable blunt trauma of the spinal cord and treated with sub-atmospheric pressure.

For these studies of a permanent injury, 36 rats with the dura intact completed the study and were analyzed. Eleven (11) vacuum treated animals started the study, with one animal removed at five weeks and one at eight weeks due to urinary tract infections and kidney failure. Thus, 9 vacuum treated animals completed the 12 week study. Twenty seven control animals started and completed the study. The vacuum treated animals exhibited a greater functional recovery ($p<0.072$) at 3 weeks post injury: BBB Score=12.818+/−1.401 (n=11) vacuum treated versus 11.704+/−2.391 (n=27) control. The vacuum treated animals exhibited a significantly greater functional recovery ($p<0.001$) at 4 weeks post injury: BBB Score 13.625+/−1.303 (n=11) vacuum treated versus 11.500+/−0.707 control (n=27). FIGS. 6 and 7. The recovery of the vacuum treated animals plateaued, and the recovery levels of the control animals gradually approached the level of the vacuum treated animals. FIGS. 6 and 7. (Note, some animals were studied for three weeks (generally earlier in the study) while some were observed for 12 weeks for functional recovery.)

In addition to the BBB assessments, two animals with intact dura were analyzed for a change in the cross sectional area (e.g., in $mm^2$) of the spinal cord by pre- and post-injury MRI scans (with the post-injury scan performed post-treatment for the vacuum treated animals) using the procedures listed above for this experiment. Of the four animals produced for this analysis, only one vacuum treated animal did not have any technical or impaction error and could he used. Of the control animals, one had a minor height error which occurred when the release pin of the spinal cord contusion system was pulled from its housing; all other control animals had significant impaction errors which precluded analysis of the cross sectional area of the spinal cord. The machine recorded height from which the weight was dropped for the vacuum treated rat was 24.8 mm and for the control rat was 25.782 mm.

Figure 8:
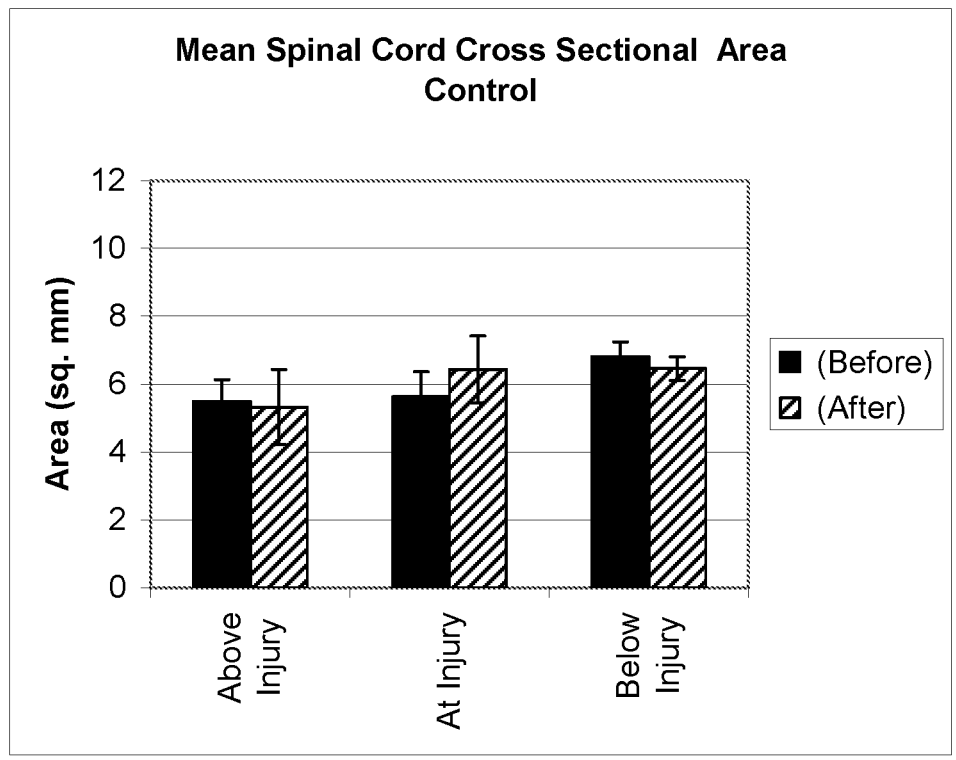
FIG. 8 illustrates the cross-sectional area of the spinal cord as a function of time for control animals exposed to non-recoverable blunt trauma of the spinal cord.

Turning to FIG. 8, the control animal showed a slight increase in cross sectional area as the scans went down (tail-ward) the spine. This was evident for both the pre-impaction scan and the post-impaction scan. At both the above-injury and below-injury sites, the cross sectional area was not significantly different between the pre-impaction scan and the post-impaction scan. The above-injury pre-impaction mean was 5.49 $mm^2$+/−0.2 (n=5) versus a post impaction mean of 5.32 $mm^2$+/−0.23 (n=4): p<0.211) (The below-injury pre-impaction mean was 6.81 $mm^2$+/−0.25 (n=3) versus a post-impaction mean of 6.46 $mm^2$+/−0.78 (n=4): p<0.464) However, at the site of impaction, the post-impaction cross sectional area for the control animal was significantly larger (p<0.001) than the pre-impaction cross sectional area: mean of pre-impaction area of 5.63 $mm^2$+/−0.24 (n=5 scans) versus mean post-impaction area of 6.43 $mm^2$+/−0.32 (n=4 scans). This was most likely due to swelling of the cord due to the limits of the dura, as the bone which would be the limiting factor on diameter of the cord had been removed.

Figure 9:
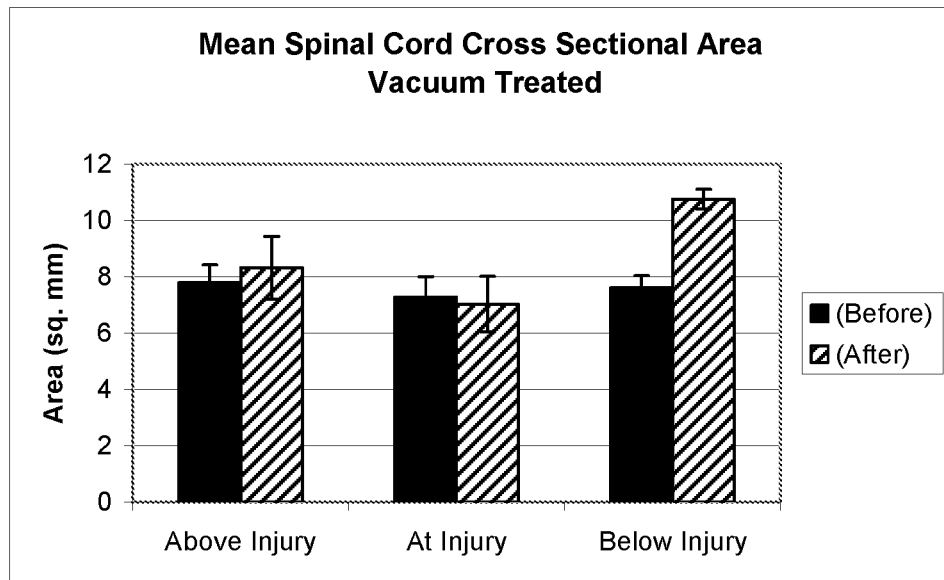
FIG. 9 illustrates the cross-sectional area of the spinal cord as a function of time for animals exposed to non-recoverable blunt trauma of the spinal cord and treated with sub-atmospheric pressure.

Unlike the control animal, the vacuum treated animal did not show an increase in mean diameter of the cord at the site of the injury after vacuum treatment, FIG. 9. The mean pre-impaction area at the level of the injury was 7.28 $mm^2$+/−0.73 (n=4 scans) versus a mean post-treatment area of 7.03 $mm^2$+/−0.99 (n=4 scans) (p<0.73). The similarity in the size of the spinal cord pre-impaction and post-treatment at the site of the injury was most likely due to removal of fluid from within the dura, thus maintaining the initial diameter of the cord.

The pre-impaction and post-treatment scans at the above-injury area were similar (not significantly different). The pre-impaction above-injury area was 7.79+/−0.64 (n=3 scans) versus post-treatment of 8.33+/−1.11 (n=5 scans) (p<0.48). For the scans of the vacuum treated animal below-injury, the post-treatment cross sectional area of the cord was significantly larger than the pre-impaction cross sectional area: Pre-impaction area of 7.61+/−0.43 (n=4 scans) versus post-treatment area of 10.76+/−0.35 (n=4 scans), p<0.001. A possible explanation for the increase in below-injury cross sectional area of the cord may be attributable to venous congestion. Alternatively, the applied vacuum may have actively withdrawn cerebrospinal fluid from around the cord, allowing the cord to expand to fill the area of the spinal canal within the vertebral bodies. This expansion would act to minimize the intra-dura pressure and help to preserve cell viability.

These and other advantages of the present invention will be apparent to those skilled in the art from the foregoing specification. Accordingly, it will be recognized by those skilled in the art that changes or modifications may be made to the above-described embodiments without departing from the broad inventive concepts of the invention. It should therefore be understood that this invention is not limited to the particular embodiments described herein, but is intended to include all changes and modifications that are within the scope and spirit of the invention as set forth in the claims.

What is claimed is:

1. An apparatus for treating damaged spinal cord tissue, comprising:
    a bio-incorporable material having a structure configured to deliver and distribute sub-atmospheric pressure to the spinal cord tissue to be treated, the bio-incorporable material having a selected surface for placement proximate the damaged spinal cord tissue and configured to prevent the growth of tissue therein;
    a vacuum source for producing a sub-atmospheric pressure disposed in gaseous communication with the bio-incorporable material for distributing the sub-atmospheric pressure through the bio-incorporable material to the spinal cord tissue to be treated;
    a cover configured to cover the damaged spinal cord tissue to the maintain sub-atmospheric pressure under the cover at the damaged spinal cord tissue; and
    an in situ suture operably connected to the vacuum source to further maintain the sub-atmospheric pressure under the cover at the damaged spinal cord.

2. An apparatus according to claim 1, wherein the bio-incorporable material itself comprises at least one surface that is sealed to prevent the transmission of sub-atmospheric pressure therethrough out of contact with spinal cord to be treated.

3. An apparatus according to claim 1, comprising an airtight dressing configured to cover the suture to maintain sub-atmospheric pressure at the damaged spinal cord tissue.

4. An apparatus according to claim 1, wherein the cover comprises a self-adhesive sheet.

5. An apparatus according to claim 1, wherein the vacuum source comprises a vacuum pump.

6. An apparatus according to claim 1, wherein the bio-incorporable material has a multi-layer structure that includes a non-ingrowth layer at the selected surface and includes an additional layer of a material different from the non-ingrowth layer.

7. An apparatus according to claim 6, wherein the additional layer is structured to promote a formation of granulation tissue.

8. An apparatus according to claim 1, wherein the bio-incorporable material is structured promote a formation of granulation tissue at a location away from the selected surface.

9. An apparatus according to claim 1, wherein the bio-incorporable material comprises a combination of polycaprolactone, polyglycolic acid, and polylactic acid.

10. The apparatus according to claim 1, wherein the vacuum source includes a tube in gaseous communication with the bio-incorporable material.

* * * * *